US008667965B2

(12) United States Patent
Gunaratnam et al.

(10) Patent No.: US 8,667,965 B2
(45) Date of Patent: Mar. 11, 2014

(54) MASK CUSHION AND FRAME ASSEMBLY

(75) Inventors: Michael K. Gunaratnam, Marsfield (AU); Gregory S. Smart, Randwick (AU); Philip R. Kwok, Chatswood (AU)

(73) Assignee: RedMed Limited, Bella Vista, New South Wales ( * ) Notice: Subject to any disclaimer, the term of this patent is extended or adjusted under 35 U.S.C. 154(b) by 513 days.

(21) Appl. No.: 12/314,975

(22) Filed: Dec. 19, 2008

(65) Prior Publication Data

US 2009/0114227 A1 May 7, 2009

Related U.S. Application Data

(60) Continuation of application No. 11/297,410, filed on Dec. 9, 2005, now Pat. No. 7,487,777, which is a continuation of application No. 10/751,926, filed on Jan. 7, 2004, now Pat. No. 7,021,311, which is a division of application No. 10/123,484, filed on Apr. 17, 2002, now Pat. No. 6,796,308, which is a continuation of application No. 09/501,004, filed on Feb. 9, 2000, now Pat. No. 6,412,487, which is a continuation-in-part of application No. 09/498,705, filed on Feb. 7, 2000, now Pat. No. 6,491,034, and a continuation-in-part of application No. 09/316,227, filed on May 21, 1999, now Pat. No. 6,513,526, and a continuation-in-part of application No. 29/101,860, filed on Mar. 12, 1999, now Pat. No. Des. 428,139, and a continuation-in-part of application No. 29/101,861, filed on Mar. 12, 1999, now Pat. No. Des. 430,663, and a continuation-in-part of application No. 29/101,862, filed on Mar. 12, 1999, now Pat. No. Des. 428,988, and a continuation-in-part of application No. 29/115,618, filed on Dec. 16, 1999, now Pat. No. Des. 443,355.

(30) Foreign Application Priority Data

Dec. 9, 1998 (AU) .................................. 3922/1998
Dec. 9, 1998 (AU) .................................. 3923/1998
Dec. 9, 1998 (AU) .................................. 3924/1998
Feb. 9, 1999 (AU) .................................. PP8550
Jun. 18, 1999 (AU) .................................. 1916/99
Jun. 18, 1999 (AU) .................................. PQ1029
Jun. 18, 1999 (AU) .................................. PQ1040

(51) Int. Cl.
*A62B 18/02* (2006.01)
*A62B 9/04* (2006.01)

(52) U.S. Cl.
USPC ............. 128/207.13; 128/206.21; 128/202.27

(58) Field of Classification Search
USPC ............. 128/205.25, 206.21, 206.23, 206.24, 128/206.26–206.28, 207.11, 207.13, 202.27
See application file for complete search history.

(56) References Cited

U.S. PATENT DOCUMENTS 35,724 A 6/1862 Wilcox
463,351 A 11/1891 Elliott
(Continued)

FOREIGN PATENT DOCUMENTS

CA 88122 11/1999
DE 297 21 766 U1 3/1998
(Continued)

OTHER PUBLICATIONS

ResMed, Mask Systems Product Brochure, 2 pages, Sep. 1992.
Respironics, Inc. "Nasal Mask System Silicone Contour Mask" Product Instructions, 2 pages, Jun. 1997.
Japanese Office Action English Translation for JP 2000-029094, 3 pages.

(Continued)

*Primary Examiner* — Kristen Matter
(74) *Attorney, Agent, or Firm* — Nixon & Vanderhye, PC

(57) ABSTRACT

A respiratory mask assembly includes a rigid mask frame and a cushion. A clip secures the cushion to the frame.

53 Claims, 19 Drawing Sheets

(56) References Cited

U.S. PATENT DOCUMENTS

| | | |
|---|---|---|
| 715,611 A | 12/1902 | Schenker et al. |
| 716,530 A | 12/1902 | Giddens |
| 812,706 A | 2/1906 | Warbasse |
| 1,333,075 A | 3/1920 | Hill et al. |
| 1,381,826 A | 6/1921 | Hansen |
| 1,653,572 A | 12/1927 | Jackson |
| 1,672,165 A | 6/1928 | Lewis |
| 1,733,020 A | 10/1929 | Jones |
| 2,029,129 A | 1/1936 | Schwartz |
| 2,033,448 A | 3/1936 | James |
| 2,141,222 A | 12/1938 | Pioch |
| 2,359,506 A | 10/1944 | Battley et al. |
| 2,371,965 A | 3/1945 | Lehmberg |
| 2,454,103 A | 11/1948 | Swidersky |
| 2,638,161 A | 5/1953 | Jones |
| 2,823,671 A | 2/1958 | Garelick |
| 2,832,015 A | 4/1958 | Ortega |
| 2,893,387 A | 7/1959 | Gongoll et al. |
| 2,931,356 A | 4/1960 | Schwarz |
| 3,141,213 A | 7/1964 | Nicholas |
| 3,189,027 A | 6/1965 | Bartlett, Jr. |
| 3,474,783 A | 10/1969 | Ulmann |
| 3,494,072 A | 2/1970 | Olson |
| 3,523,534 A | 8/1970 | Nolan |
| 3,535,810 A | 10/1970 | Baehrle |
| 3,555,752 A | 1/1971 | Bogaert |
| 3,824,999 A | 7/1974 | King |
| 4,049,357 A | 9/1977 | Hamisch, Jr. |
| 4,064,875 A | 12/1977 | Cramer et al. |
| 4,111,197 A | 9/1978 | Warncke et al. |
| 4,121,580 A | 10/1978 | Fabish |
| 4,164,942 A | 8/1979 | Beard et al. |
| 4,226,234 A | 10/1980 | Gunderson |
| 4,274,404 A | 6/1981 | Molzan et al. |
| 4,380,102 A | 4/1983 | Hansson |
| 4,494,538 A | 1/1985 | Ansite |
| 4,506,665 A | 3/1985 | Andrews et al. |
| 4,549,334 A | 10/1985 | Miller |
| 4,580,556 A | 4/1986 | Kondur |
| 4,606,340 A | 8/1986 | Ansite |
| 4,622,964 A | 11/1986 | Flynn |
| 4,633,972 A | 1/1987 | DeRocher |
| 4,783,029 A | 11/1988 | Geppert et al. |
| 4,794,921 A | 1/1989 | Lindkvist |
| 4,807,617 A | 2/1989 | Nesti |
| 4,809,692 A | 3/1989 | Nowacki et al. |
| 4,835,820 A | 6/1989 | Robbins, III |
| 4,841,953 A | 6/1989 | Dodrill |
| 4,870,963 A | 10/1989 | Carter |
| 4,875,714 A | 10/1989 | Lee |
| 4,898,174 A | 2/1990 | Fangrow, Jr. |
| 4,899,614 A | 2/1990 | Kataumi |
| 4,974,586 A | 12/1990 | Wandel et al. |
| 4,981,134 A | 1/1991 | Courtney |
| 4,997,217 A | 3/1991 | Kunze |
| 5,003,633 A | 4/1991 | Itoh |
| 5,005,568 A | 4/1991 | Loescher et al. |
| 5,062,420 A | 11/1991 | Levine |
| 5,080,094 A | 1/1992 | Tayebi |
| 5,136,760 A | 8/1992 | Sano et al. |
| 5,215,336 A | 6/1993 | Worthing |
| 5,243,971 A | 9/1993 | Sullivan et al. |
| 5,253,641 A | 10/1993 | Choate |
| 5,311,862 A | 5/1994 | Blasdell et al. |
| 5,398,673 A | 3/1995 | Lambert |
| 5,438,981 A | 8/1995 | Starr et al. |
| 5,501,214 A | 3/1996 | Sabo |
| 5,538,001 A | 7/1996 | Bridges |
| 5,645,049 A | 7/1997 | Foley et al. |
| 5,647,355 A | 7/1997 | Starr et al. |
| 5,676,133 A | 10/1997 | Hickle et al. |
| 5,709,204 A | 1/1998 | Lester |
| 5,724,965 A | 3/1998 | Handke et al. |
| 5,794,617 A | 8/1998 | Brunell et al. |
| 5,839,436 A | 11/1998 | Fangrow et al. |
| 5,860,677 A | 1/1999 | Martins et al. |
| 5,896,857 A | 4/1999 | Hely et al. |
| 5,909,732 A | 6/1999 | Diesel et al. |
| 5,921,239 A * | 7/1999 | McCall et al. ........... 128/205.25 |
| 5,937,851 A | 8/1999 | Serowski et al. |
| 5,979,025 A | 11/1999 | Horng |
| D428,139 S | 7/2000 | Smart |
| 6,082,360 A | 7/2000 | Rudolph et al. |
| D428,988 S | 8/2000 | Smart |
| D430,663 S | 9/2000 | Smart |
| 6,119,693 A | 9/2000 | Kwok et al. |
| 6,189,532 B1 | 2/2001 | Hely et al. |
| 6,192,886 B1 | 2/2001 | Rudolph |
| 6,196,223 B1 | 3/2001 | Belfer et al. |
| D443,335 S | 6/2001 | Gunaratnam et al. |
| 6,240,605 B1 | 6/2001 | Stevens et al. |
| 6,250,375 B1 | 6/2001 | Lee et al. |
| 6,256,846 B1 | 7/2001 | Lee |
| 6,272,722 B1 | 8/2001 | Lai |
| 6,321,421 B1 | 11/2001 | Lim |
| 6,381,813 B1 | 5/2002 | Lai |
| 6,412,487 B1 | 7/2002 | Gunaratnam et al. |
| 6,449,817 B1 | 9/2002 | Hsu |
| 6,463,931 B1 | 10/2002 | Kwok et al. |
| 6,491,034 B1 | 12/2002 | Gunaratnam et al. |
| 6,513,206 B1 | 2/2003 | Banitt et al. |
| 6,513,526 B2 | 2/2003 | Kwok et al. |
| 6,520,182 B1 | 2/2003 | Kwok et al. |
| 6,532,961 B1 | 3/2003 | Kwok et al. |
| 6,615,832 B1 | 9/2003 | Chen |
| 6,691,708 B2 | 2/2004 | Kwok et al. |
| 6,701,927 B2 | 3/2004 | Kwok et al. |
| 6,796,308 B2 | 9/2004 | Gunaratnam et al. |
| 7,021,311 B2 | 4/2006 | Gunaratnam et al. |
| 2002/0153012 A1 | 10/2002 | Gunaratnam et al. |
| 2006/0130843 A1 | 6/2006 | Gunaratnam et al. |

FOREIGN PATENT DOCUMENTS

| | | |
|---|---|---|
| DE | 4 99 00 269 | 1/1999 |
| EP | 1 027 905 A3 | 8/2000 |
| ES | 145309 | 1/2000 |
| FR | 2 691 906 | 12/1993 |
| FR | 99/16 | 8/1999 |
| GB | 2080119 | 12/1998 |
| GB | 2080120 | 12/1998 |
| GB | 2080121 | 12/1998 |
| JP | 48-55696 | 10/1971 |
| JP | 59-55535 | 4/1984 |
| JP | 61-67747/86 | 5/1986 |
| JP | 7-21058/95 | 4/1995 |
| JP | 7-308381 | 11/1995 |
| JP | 9-501084 | 2/1997 |
| JP | 1105649 | 2/1999 |
| SE | 65481 | 8/2000 |
| WO | WO 80/01645 | 8/1980 |
| WO | WO 87/01950 | 4/1987 |
| WO | WO 95/04566 | 2/1995 |
| WO | WO 98/26830 | 6/1998 |
| WO | WO 98/48878 | 11/1998 |
| WO | WO 99/30760 | 6/1999 |
| WO | WO 00/38772 | 7/2000 |

OTHER PUBLICATIONS

ResCare Limited, "Sullivan™ Nasal CPAP System, *Nose Mask Clip—User Instructions*", May 1990, 1pg.

Respironics, Inc., "Nasal Mask System Silicone Contour Mask," Product Instructions, 2 pages, Jun. 1997.

The American Heritage Dictionary, Second College Edition, 1982, 3 pages.

Office Action issued in U.S. Appl. No. 13/396,002, issued on Oct. 8, 2013.

U.S. Patent Application Publication No. 2012/0180794, filed on Feb. 14, 2012, Gregory Scott Smart, Jul. 2012.

* cited by examiner

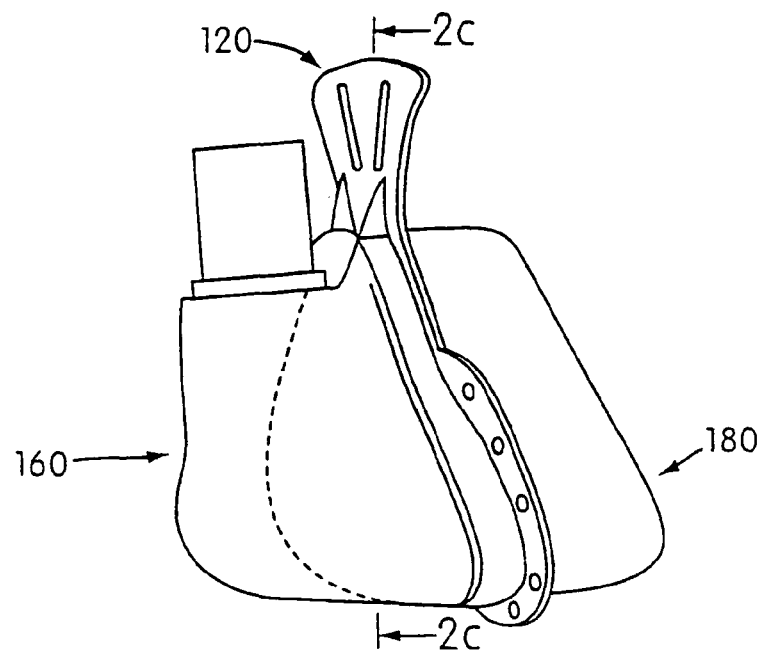
FIG. 2a
PRIOR ART
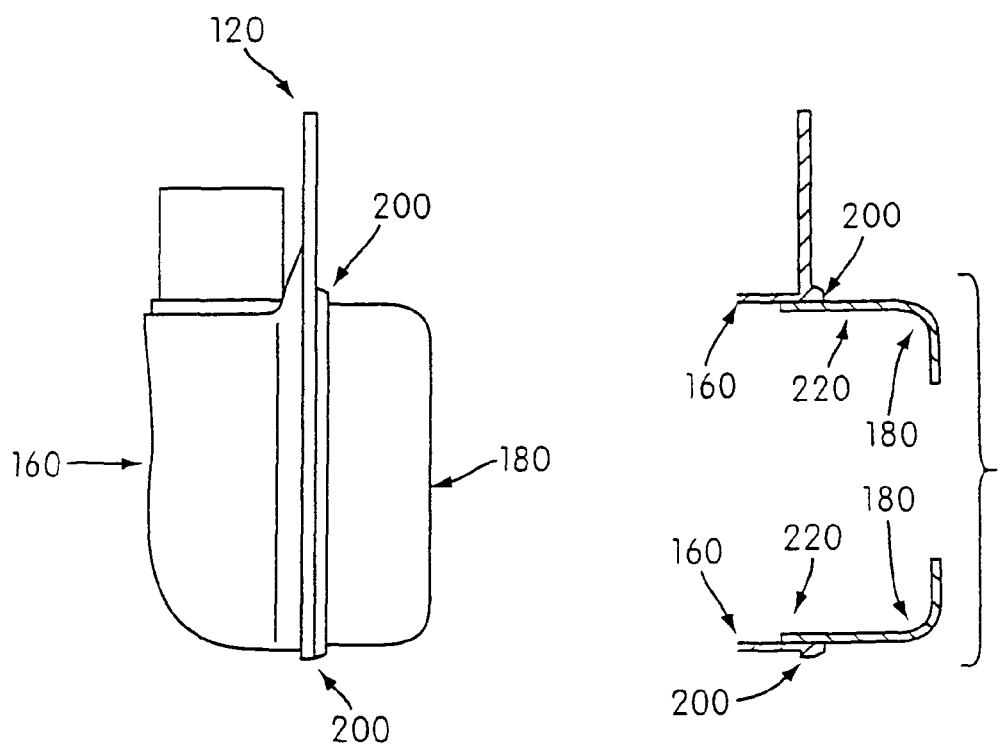
FIG. 2b
PRIOR ART
FIG. 2c
PRIOR ART

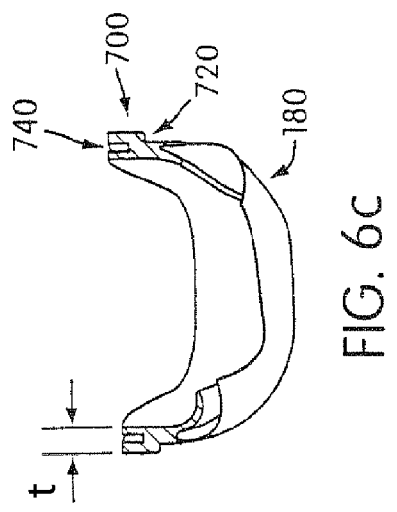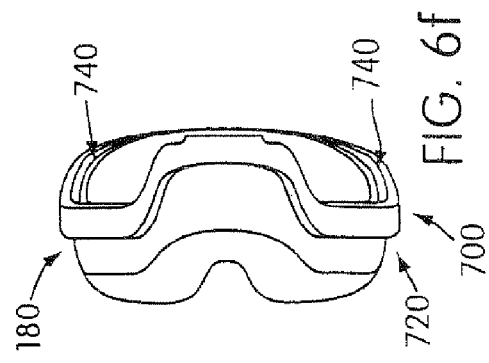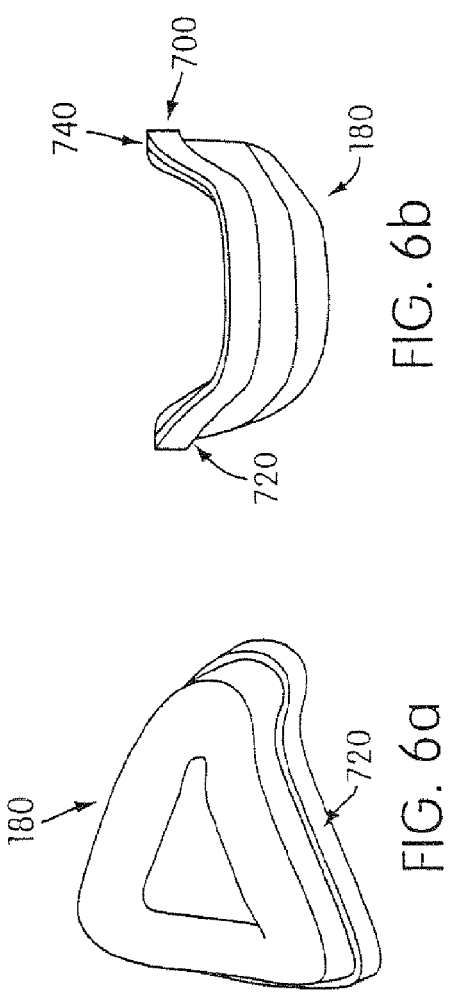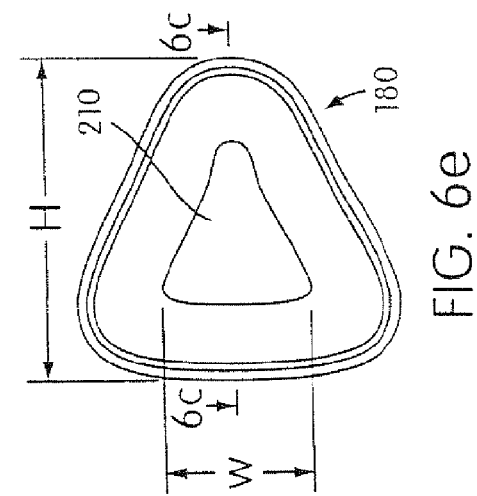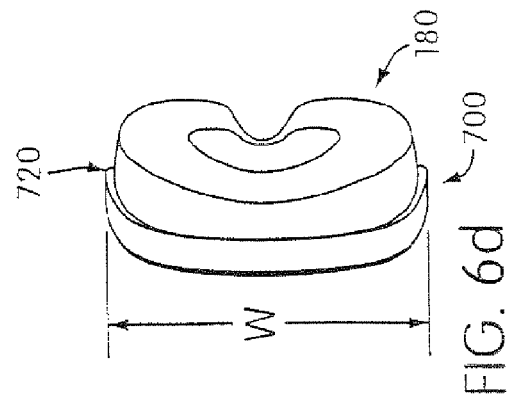

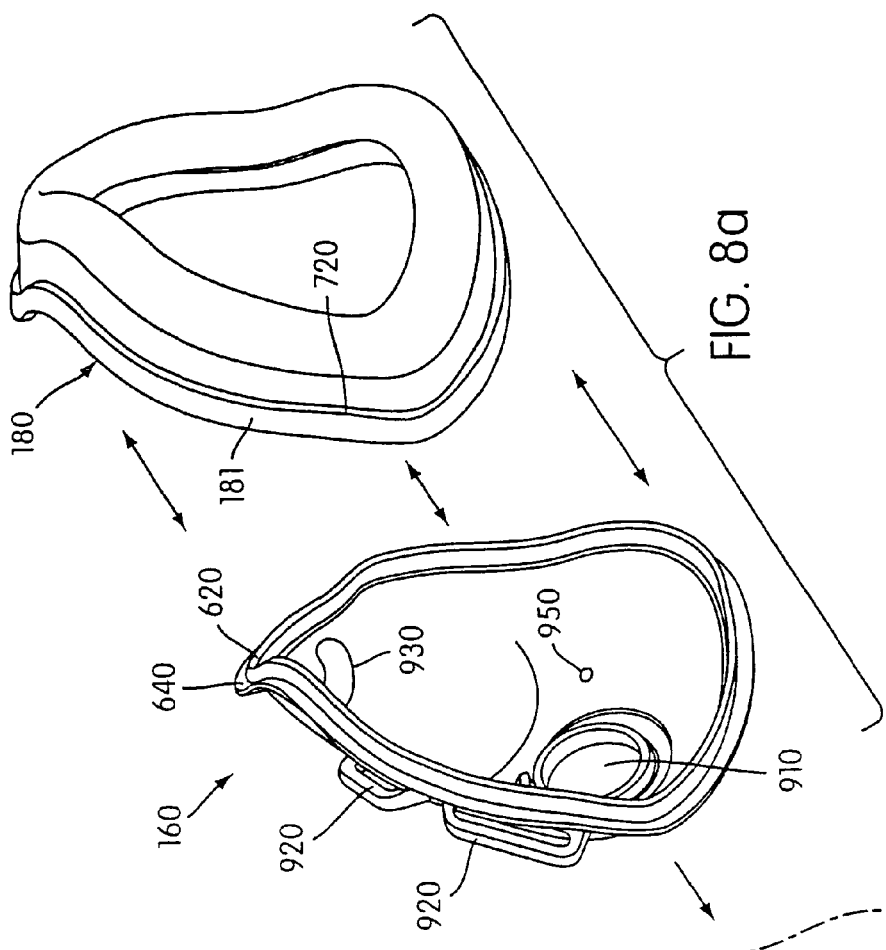

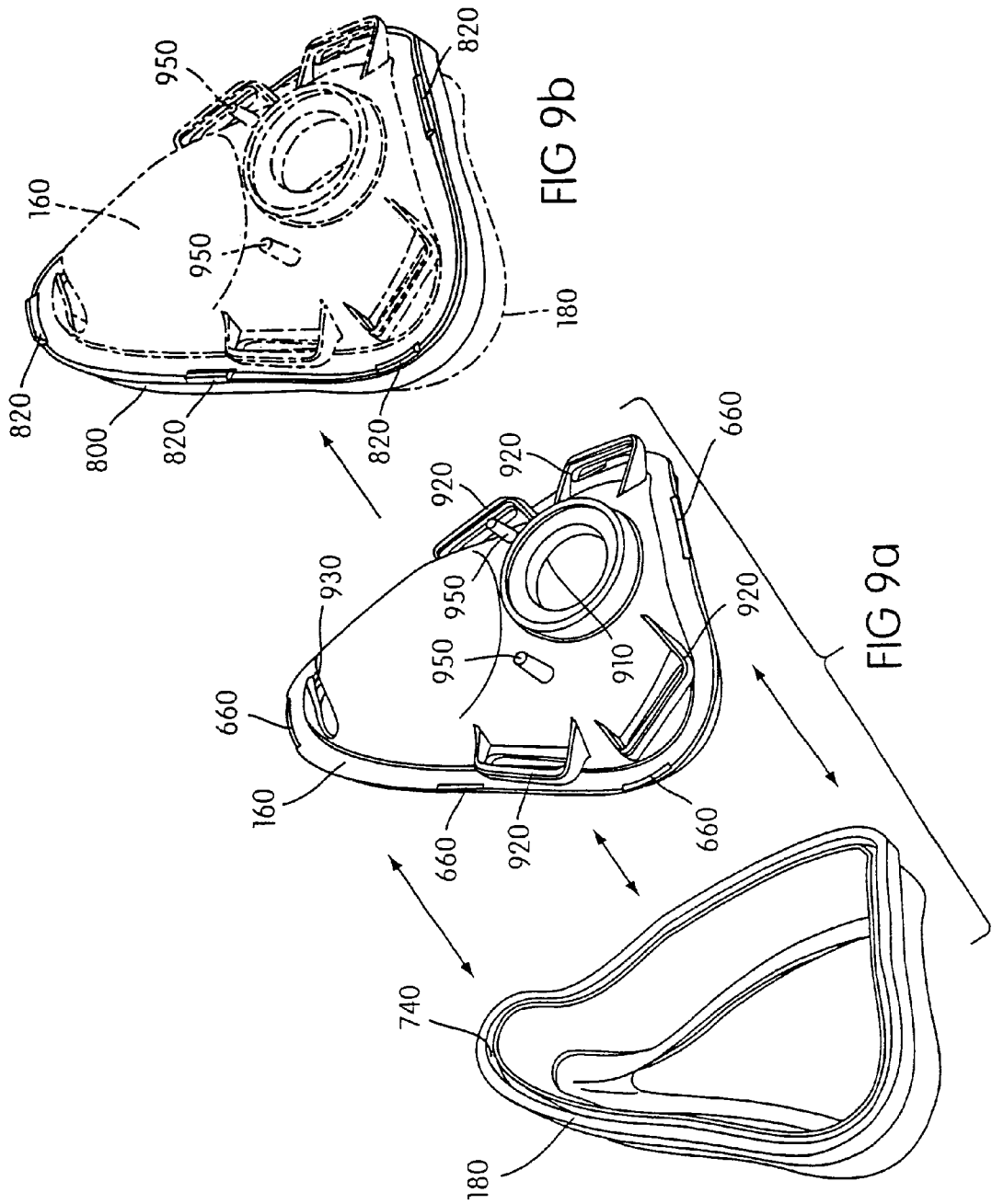

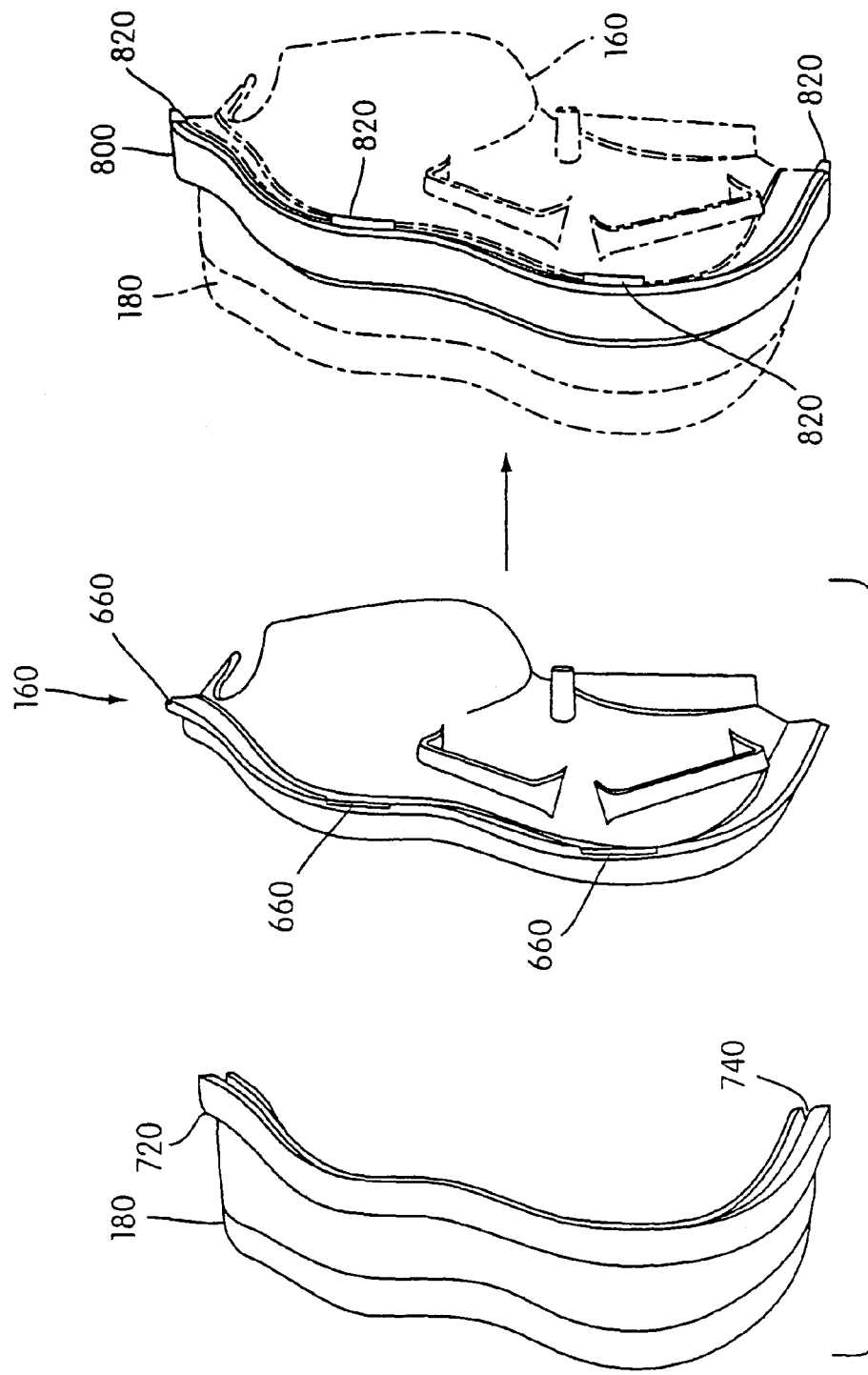

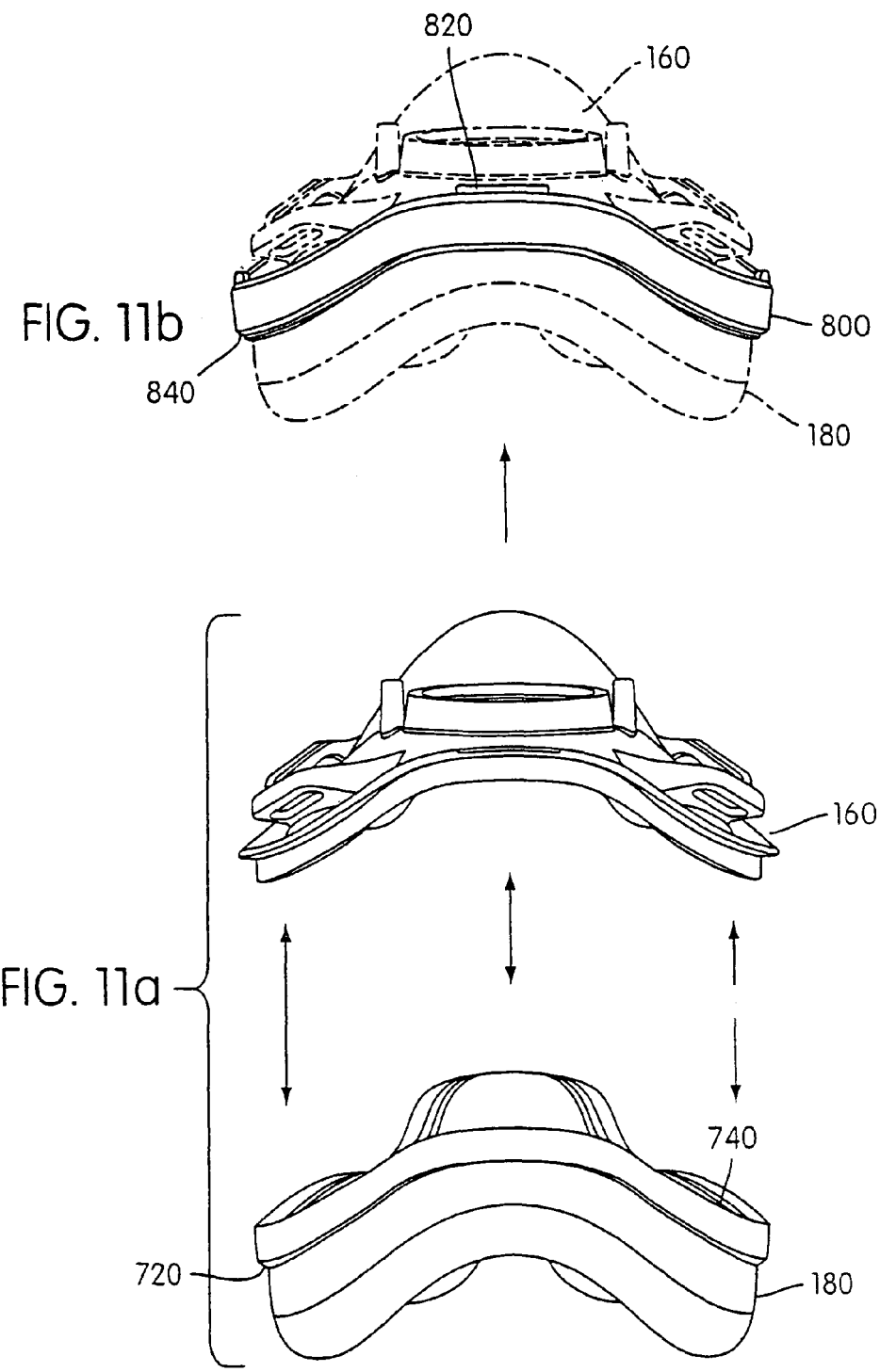

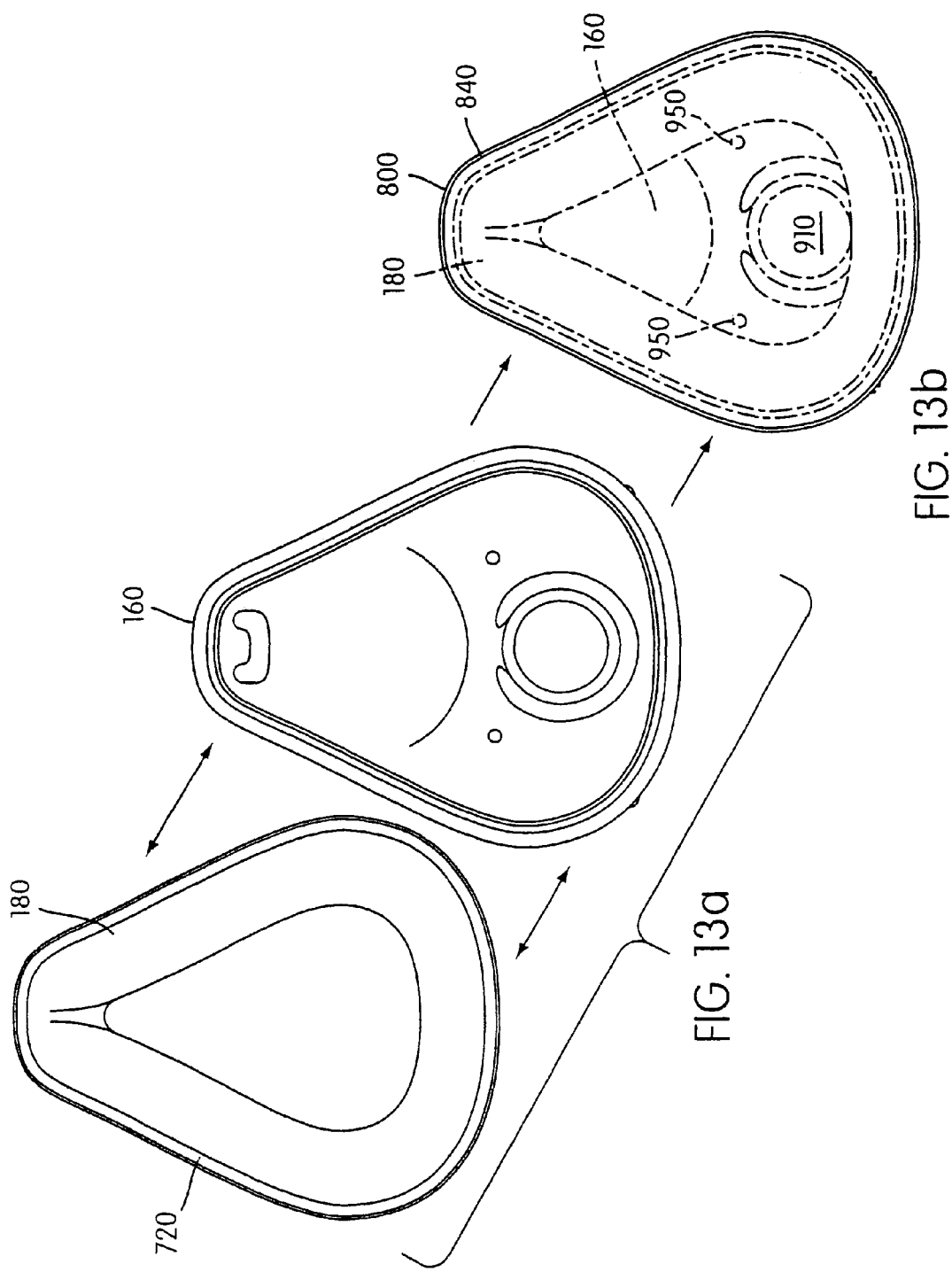

MASK CUSHION AND FRAME ASSEMBLY

CROSS REFERENCE TO RELATED APPLICATIONS

This application is a Continuation of U.S. application Ser. No. 11/297,410, filed Dec. 9, 2005, now U.S. Pat. No. 7,487,777, which is a Continuation of U.S. application Ser. No. 10/751,926, filed Jan. 7, 2004, now U.S. Pat. No. 7,021,311, which is a Divisional of U.S. application Ser. No. 10/123,484, filed Apr. 17, 2002, now U.S. Pat. No. 6,796,308, which is a Continuation of U.S. application Ser. No. 09/501,004, filed Feb. 9, 2000, now U.S. Pat. No. 6,412,487, which is a Continuation-in-Part (CIP) of U.S. application Ser. No. 09/498,705, filed Feb. 7, 2000, now U.S. Pat. No. 6,491,034, a CIP of U.S. application Ser. No. 09/316,227, filed May 21, 1999, now U.S. Pat. No. 6,513,526; a CIP of U.S. Design Application No. 29/101,860, filed Mar. 12, 1999, now U.S. Design Pat. No. D428,139; a CIP of U.S. Design Application No. 29/101,861, filed Mar. 12, 1999, now U.S. Design Pat. No. D430,663; a CIP of U.S. Design Application No. 29/101,862, filed Mar. 12, 1999, now U.S. Design Pat. No. D428,988; and a CIP of U.S. Design Application No. 29/115,618, filed Dec. 16, 1999, now U.S. Design Pat. No. D443,355, each of which is incorporated by reference in its entirety.

FIELD OF THE INVENTION

The invention relates to a method and apparatus for connecting a nasal or full-face mask cushion to a mask frame, where the mask is suitable for the delivery of breathable gases to a patient for the treatment of sleep disordered breathing (SDB).

BACKGROUND OF THE INVENTION

Nasal and full-face masks systems suitable for the delivery of air or other breathable gases to patients for the treatment of sleep disordered breathing may include a mask (100), a forehead support (120) and headgear (140), as depicted in FIG. 1. The mask may comprise a rigid shell (160), termed a frame, and a soft portion (180), termed a cushion. The frame may be constructed from a material such as polycarbonate, forming a cavity which overlies the patient's nose and/or mouth. The soft cushion may be constructed from a material such as silicone spacing the frame away from the patient's face to provide comfortable contact.

In the case of the Mirage® Mask (ResMed Limited), shown in FIG. 1, the headgear (140) is constructed from fabric and includes a rear portion which engages the region near the occiput of the patient, and four straps (145) which are secured to a forehead support (2 straps) and nasal mask frame (2 straps). The straps include hook and loop material, such as Velcro™ on one side. The mask frame and forehead supports include loops through which straps can pass.

In one form of known mask, the cushion and frame are glued together, as shown in FIG. 2a to 2c. FIG. 2c shows a cross-section 2c-2c through FIG. 2a. The frame (160) includes a rim portion (200) surrounding the rear aperture of the frame. There is a corresponding rim portion (220) on the cushion (180) which fits inside the rim (200) on the frame. The two rims (200, 220) are glued together. A disadvantage with this approach is that the cushion cannot easily be removed for separate cleaning from the frame. Furthermore, there is an increased manufacturing cost since gluing requires assembly time and adhesive.

In one known mask, the Modular mask system (ResMed Limited), the frame and cushion are held, together using a tongue (300) and groove (320), as depicted in FIG. 3a to 3c. The frame (160) is generally triangular in front view. In use, the front of the frame faces away from the patient and the back of the frame faces towards the patient. The rim portion (350) on the frame (160) includes an outwardly extending flange (340) and engages with a corresponding rim (360) on the cushion (180), such that the rims (350, 360) confront along a locus lying generally in the plane of the patient's face. The frame rim (350) further includes a tongue (300) which protrudes rearwardly from the back of the frame and is received in a corresponding complementary shaped groove (320) formed in rim portion (360) of the cushion (180). In addition, the rim (350) of the frame (160) and the rim (360) of the cushion (180) include aligned slots (380) through which headgear straps (145) can pass. Hence the slots (380) and straps (145) make a contribution to holding the frame (160) and cushion (180) together, in addition to the use of the tongue (300) and groove (320).

In another known mask, a tongue and groove mechanism is used to hold the frame (160) and cushion (180) together, and the tongue (500), which is positioned on the frame (160) has an irregular cross-section as depicted in FIG. 4a to 4c. The side (520) of the tongue (500) on the interior of the frame (160) is flat. The other side (540) of the tongue (500) has a lateral projection (560) approximately at right angles to the tongue (500). The groove (580) of the cushion (180) has a complimentary shape, including a lateral recess (585) for receiving projection (560). The connection relies on the elasticity of the cushion to retain the cushion in place.

The present invention aims to provide an improved arrangement.

SUMMARY OF THE INVENTION

The present invention provides a respiratory mask assembly for delivering breathable gas to a patient, comprising (i) a substantially rigid mask frame defining a cavity with a rear opening, and a rim portion surrounding said rear opening, said rim portion including a rearwardly projecting tongue, (ii) a flexible mask cushion acting to space the mask frame away from the patient's face, said cushion having a rim portion which includes a groove receiving said projecting tongue of the mask frame, and wherein an outer surface of the cushion forms a rearwardly facing shoulder, and (iii) a clip member passing over the mask cushion, having cushion retaining means engaging behind said shoulder of the cushion and securing means which engages the mask frame so as to retain the mask cushion on the mask frame.

Preferably, the clip's securing means includes at least one securing tab which engages a respective recess in the mask flame, and more preferably on a lateral flange of rim portion of the frame.

Preferably also, the clip is formed as a collar member having a plurality of tabs angularly spaced about the collar member, and the mask frame has a respective plurality of the recesses.

BRIEF DESCRIPTION OF THE DRAWINGS

FIG. 2a shows a perspective view of a form of prior art mask frame and cushion which are glued together FIG. 2b shows a side view of the mask shown in FIG. 2a.

FIG. 2c shows a cross-sectional view of the mask shown in FIG. 2a.

FIG. 3b, shows a side view of the mask shown in FIG. 3a.

FIG. 3c shows a cross-sectional view of the mask shown in FIG. 3a.

FIG. 5b shows a side view of the mask frame shown in FIG. 5a.

FIG. 6a shows a rear perspective view of a nasal mask cushion suitable for the nasal mask frame of FIGS. 5a and 5b.

FIG. 6b, shows a side view of the mask cushion shown in FIG. 6e.

FIG. 6c shows a cross-section through the mask cushion shown in FIG. 6e.

FIG. 6d shows a bottom view of the mask cushion shown in FIG. 6e.

FIG. 6e shows a view from the patient (rear) side of the mask cushion shown in FIG. 6a.

FIG. 6f shows a top view of the mask cushion shown in FIG. 6e.

FIG. 7b shows a view of the clip shown in FIG. 7a.

In FIGS. 6a to 6f and 7a to 7e dimensions are shown in millimeters.

FIG. 8a is a rear perspective exploded view illustrating the cushion and frame according to a full face mask embodiment.

FIG. 8b is an assembled view of the cushion and frame of FIG. 8a, along with the clip.

FIG. 9a is a front perspective exploded view illustrating the cushion and frame according to the full face mask embodiment.

FIG. 9b is an assembled view of the cushion and frame, along with the clip.

FIG. 10a is an exploded side view of the cushion and frame according to the full face mask embodiment.

FIG. 10b is an assembled view of the cushion and frame, along with the clip.

FIG. 11a is an exploded bottom view of the frame and cushion according to the full face mask.

FIG. 11b is an assembled view of the cushion and frame, along with the clip.

FIG. 13a is an exploded rear view of the frame and cushion according to the full face mask.

FIG. 13b is an assembled view of the cushion and frame, along with the clip.

DETAILED DESCRIPTION OF THE INVENTION

The method and apparatus for securing a cushion to a mask frame includes a combination of tongue and groove mechanism and a clip in the form of a collar member which passes over and engages both the cushion and the frame.

Figure 5A:
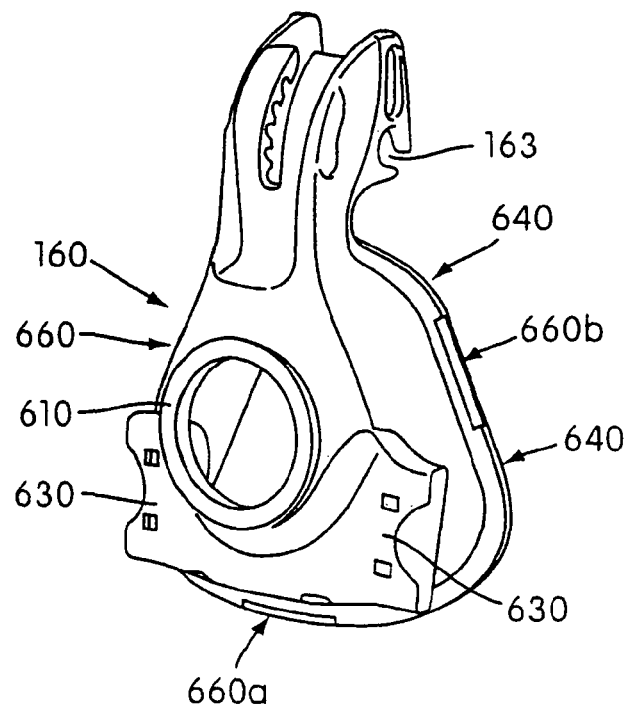
FIG. 5a shows a front perspective view of a nasal mask frame according to an embodiment of the invention.
Figure 5B:
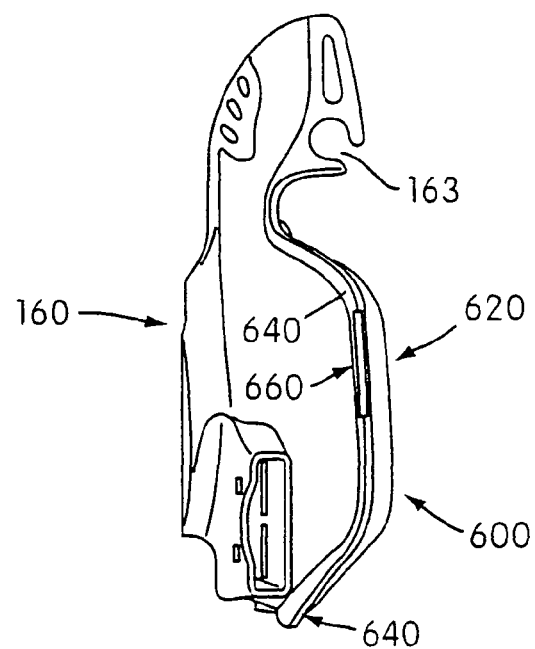
Figure 5C:
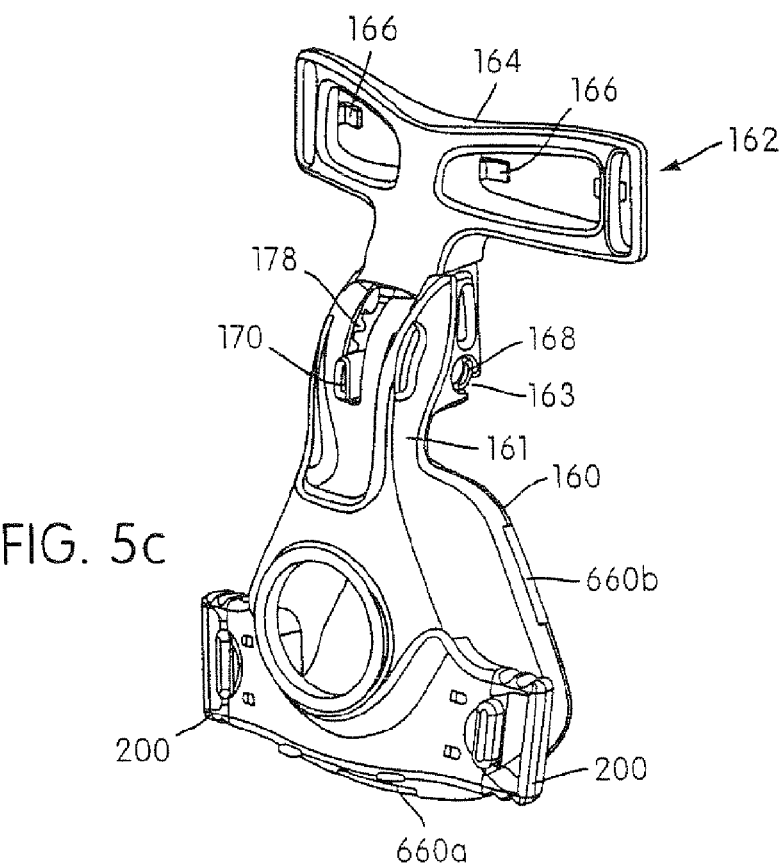
FIG. 5c is a front perspective view of a nasal mask frame and adjustable forehead support according to an embodiment.
Figure 5D:
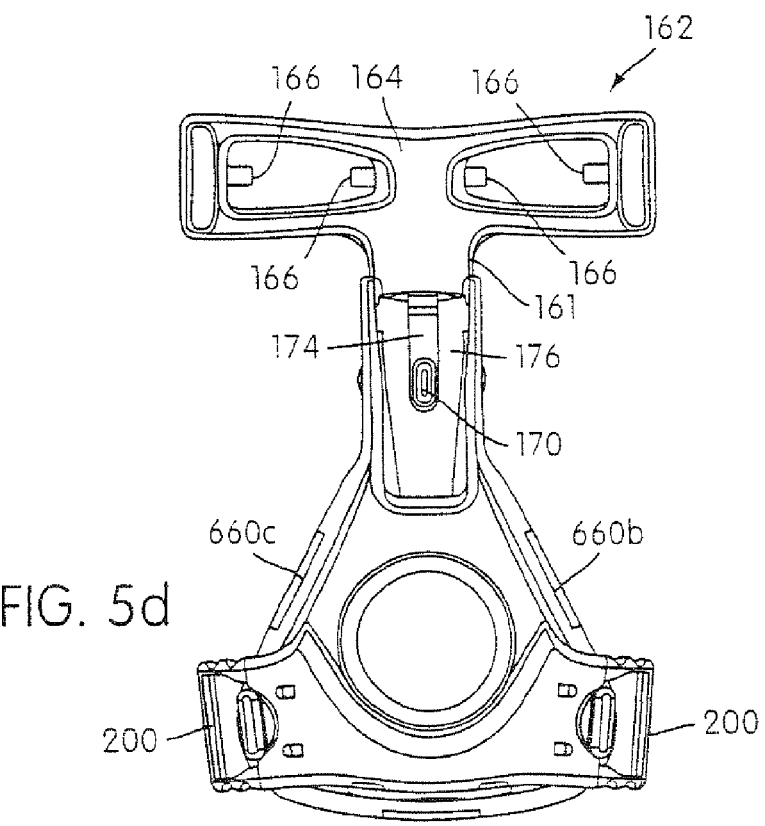
FIG. 5d is a front view of the embodiment of FIG. 5c.
Figure 5E:
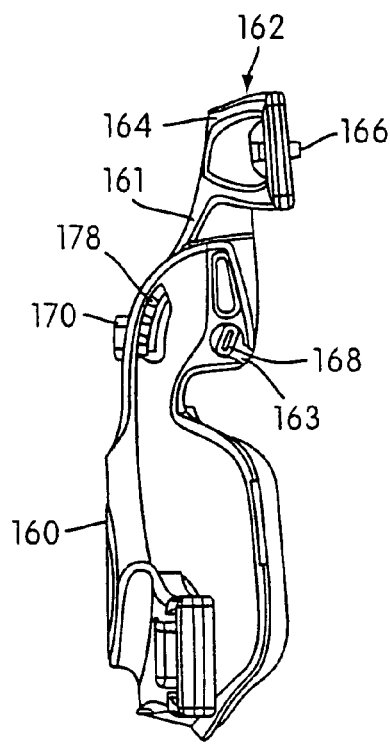
FIG. 5e is a side view of the embodiment of FIG. 5c.

A nasal mask frame including a rim portion according to an embodiment of the invention is shown in FIG. 5a and FIG. 5b. The frame (160) is constructed as a substantially rigid shell of polycarbonate or similar transparent plastics material, and incorporates a gas inlet aperture (610) for connection to a gas delivery conduit (not shown) of a patient gas delivery system.

The frame (160) is generally triangular in front view, covering the patient's nose, and defines a cavity which is open at its rear, the rear opening being surrounded by a rim portion (600) which follows a locus approximating the contours of a patient's face.

On the front surface of the frame, are strap connection points (630) for connection of the mask to patient headgear. Connectors (200) are shown in FIGS. 5c-5f.

As best seen in FIG. 5b, the rim portion (600) of the frame (160) includes a rearwardly projecting tongue (620) and a lateral flange (640). The tongue (620) has an approximately rectangular cross-section. The flange (640) is approximately perpendicular to the tongue (620) and also has an approximately rectangular cross-section. The flange (640) includes three recesses (660) angularly spaced about the rim. Of these, only the bottom recess (660a) and one side recess (660b) are visible in the view of the frame (160) shown in FIG. 5a. The recesses are of an approximately rectangular shape, formed in the front surface of flange (640) adjacent its edge.

FIGS. 5c-5f show additional views of the frame (160). As compared to FIGS. 5a-5b, FIGS. 5c-5f also show an adjustable forehead support (162) connected to the frame (160). The adjustable forehead support (162) includes a bridge portion (164) adapted to locate at least one and preferably two spaced apart pads (not shown) adapted to contact the forehead of the patient. Projection members (166) are formed on the bridge portion (164), and can be used to secure the forehead pads to the bridge portion (164).

The forehead support (162) is coupled to the frame (160) in this example using a pair of small shafts (168) formed on the forehead support (162). The frame (160) includes an extension (161) having a pair of keyed receiving slots (163) to receive the shafts (168). Adjustment is carried out by use of an actuator button (170) coupled in cantilever fashion to the end of a tab (172) formed on the forehead support (162). The actuator button (170) protrudes from the patient side of the extension (161) through a slot (174) (FIG. 5*d*) formed in the extension (161), thereby exposing the actuator button (170) to the exterior surface (176) of the extension (161), which facilitates access by the patient. The frame (160) is provided with a number of teeth (178), e.g. at least three, to enable the forehead support (162) to be positioned in a corresponding number of positions, so the mask can accommodate patients having a wide scope of facial geometries.

Figure 5F:
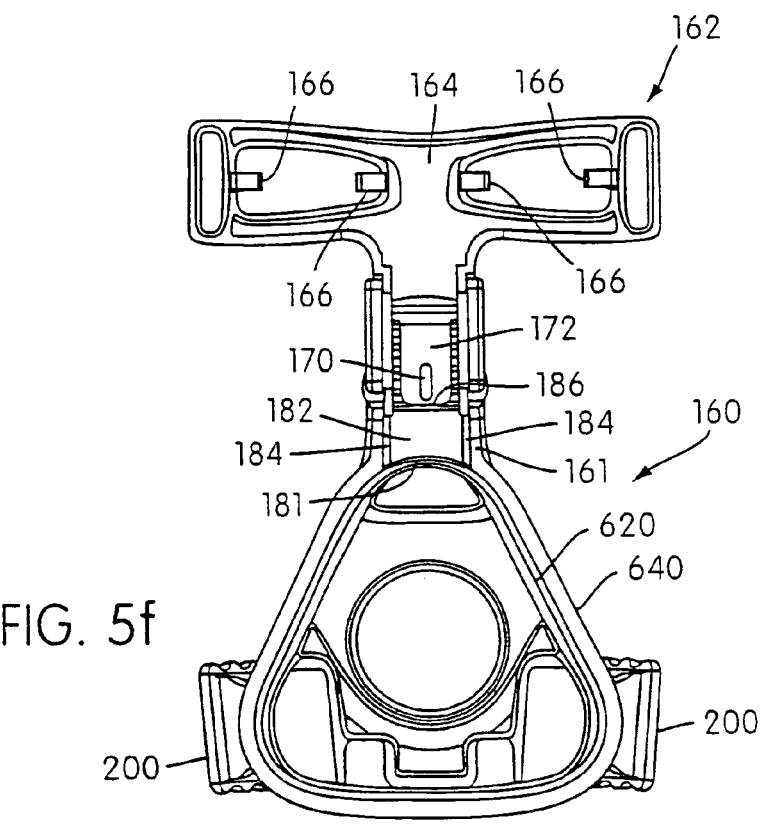
FIG. 5f is a rear view of the embodiment of FIG. 5c.

FIG. 5*f* shows that the tongue (620) and the flange (640) have a generally triangular shape. An apex (181) of the tongue (620) is provided adjacent to a point where the extension (161) extends upwardly above the main part of the frame (160). A receiving space (182) is defined in a region of the extension (161) just above the apex (181) of the tongue (620). Sidewalls (184) define the side boundaries of the receiving space (182), while the end (186) of the tab (172) defines the upper boundary of the receiving space (182). The purpose of the receiving space (182) will be described below in conjunction with FIGS. 7*a*-7*e*.

The thickened rim portion (700) of the cushion has an inwards step (720) in its outer surface, forming a rearwardly facing shoulder.

The cushion is formed of soft material such as silicone, and projects rearwardly of the mask frame so as to space the rigid frame away from the patient's face. The width (W) of the cushion is about 71.2 mm, as shown in FIG. 6*d*. The width (W) of the aperture 210 is about 31.7 mm. The height (H) is about 72.1 mm. The height of the aperture 210 is about 36.7 mm. The thickness (t) of the lower sidewall is about 6.6 mm, as shown in FIG. 6*c*.

A clip (800) according to an embodiment of the invention, suitable for a nasal mask, is shown in FIG. 7*a* to 7*e*. The clip is formed as a collar of a complementary shape to the rims of the mask cushion (700) and frame (600) and fits over them. The clip is constructed from polycarbonate or similar material. In the illustrated embodiment the clip (800) includes three securing tabs (820) such that inwards projections on the detents are formed as resilient detents which extend past the outer edge of flange (640) to be retained in recesses (660) on the front of the flange (640). To disengage, for example for cleaning of the mask assembly or replacement of the cushion, the detents may be forced outwardly against their natural resilience to release from the recesses (660) and ride over the outer edge of flange (640). In other embodiments, other numbers of securing tabs may be used.

The rear of the clip has an inwards flange (840) which engages behind the shoulder (720) of the cushion so as to hold the cushion securely in position on the frame when the tabs (820) are engaged on the rim (600) of the frame.

Figure 7E:
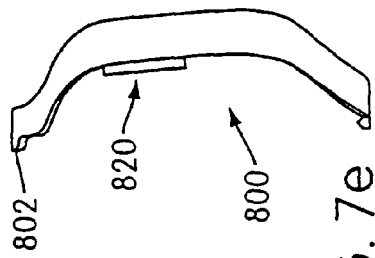
FIG. 7e shows a side view of the clip shown in FIG. 7b.
Figure 7B:
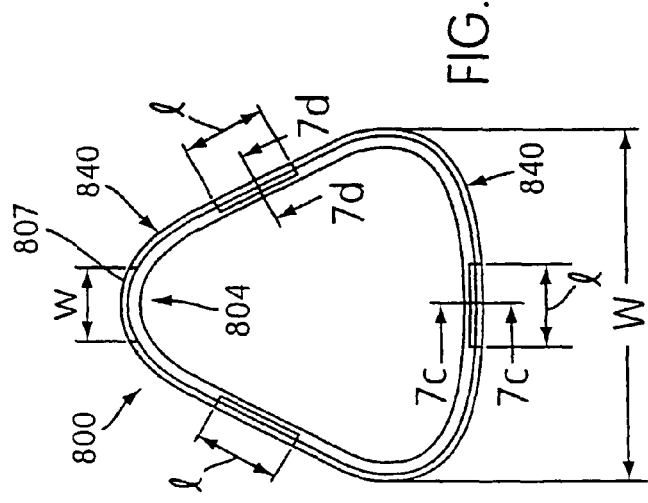
Figure 7D:
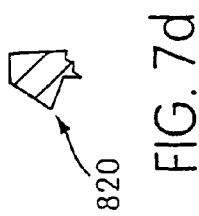
FIG. 7d shows an enlarged section 7d-7d through the clip in a position indicated in FIG. 7b.
Figure 7A:
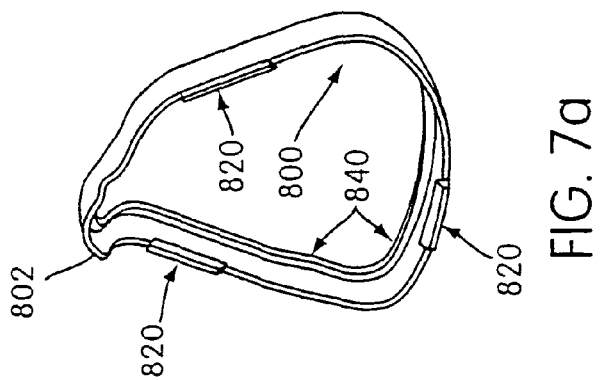
FIG. 7a shows a perspective view of a clip suitable for the nasal mask frame of FIGS. 5a and 5b and the nasal mask cushion of FIGS. 6a to 6f.
Figure 7C:
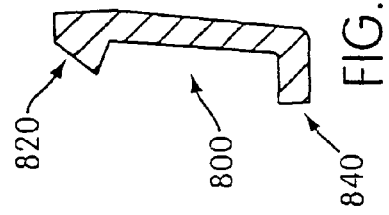
FIG. 7c shows an enlarged section 7c-7c through the clip in the position indicated in FIG. 7b.
Figure 12B:
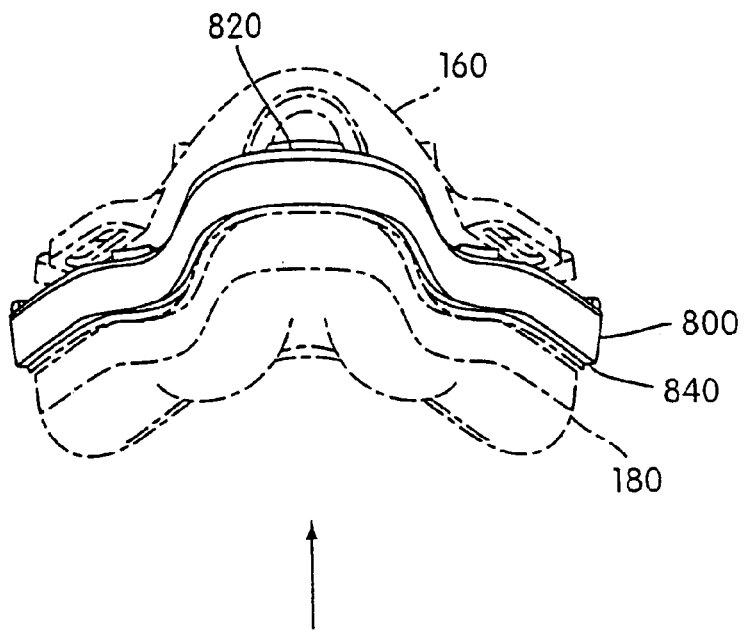
FIG. 12b is an assembled view of the cushion and frame, along with the clip.
Figure 12A:
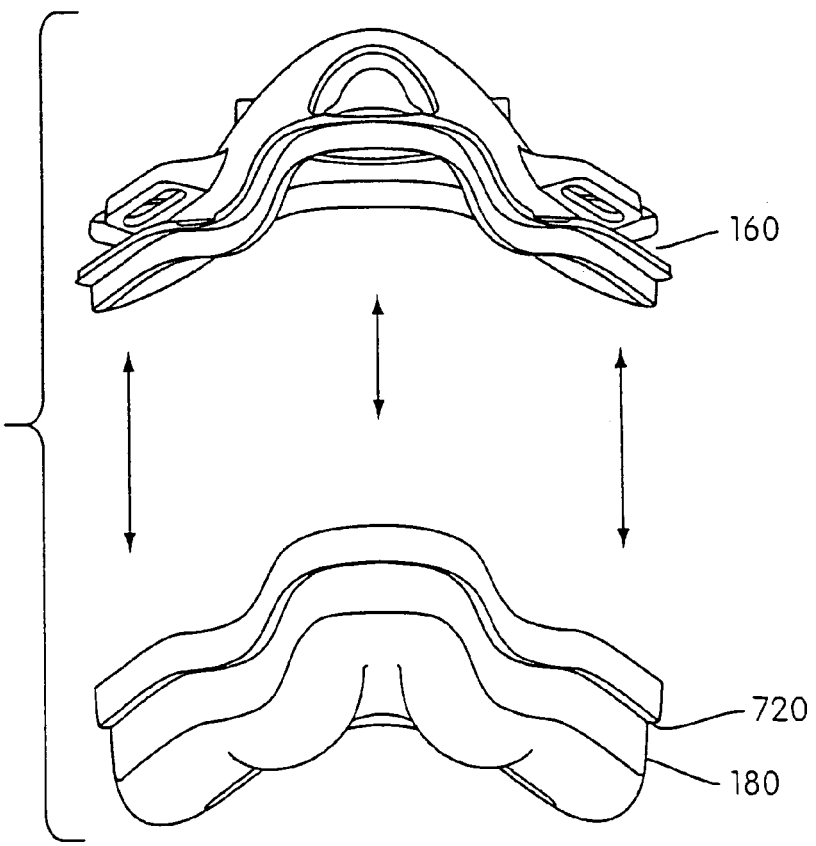
FIG. 12a is an exploded top view of the frame and cushion according to the full face mask.

Furthermore, the clip (800) includes a guide projection (802) located at an apex (804) of the clip (800), as shown in FIGS. 7*a*, 7*b* and 7*e*. The projection (802) is positioned diametrically across from the lowermost securing tab (820), as best seen in FIG. 7*b*. The projection (802) has an arcuate shape that generally matches the curve of the clip (800) at the apex (804) thereof.

As shown in FIG. 7*b*, the length (l) of each of the securing tabs is about 18.0 mm. The width (w) of the guide projection (802) is about 15.5 mm, and the width (W) of the base of the clip (800) is about 73.83±0.5 mm.

The guide projection (802) helps guide the clip (800) into place when the clip (800) is secured to the frame (160). In this context, the guide projection (802) is not shown as including inwardly facing detents, which distinguish the guide projection (802) from the securing tabs (820), which have inwardly facing detents. In particular, the guide projection (802) is intended to be received within the receiving space (182), which is shown in FIG. 5*f*. The guide projection (802) has a shape that is complementary to the shape of the apex (181) of the tongue (620) of the frame (160). The width (w) of the guide projection (802) is dimensioned such that it fits between sidewalls (184) of the extension (161).

Figures 14A, 14B:
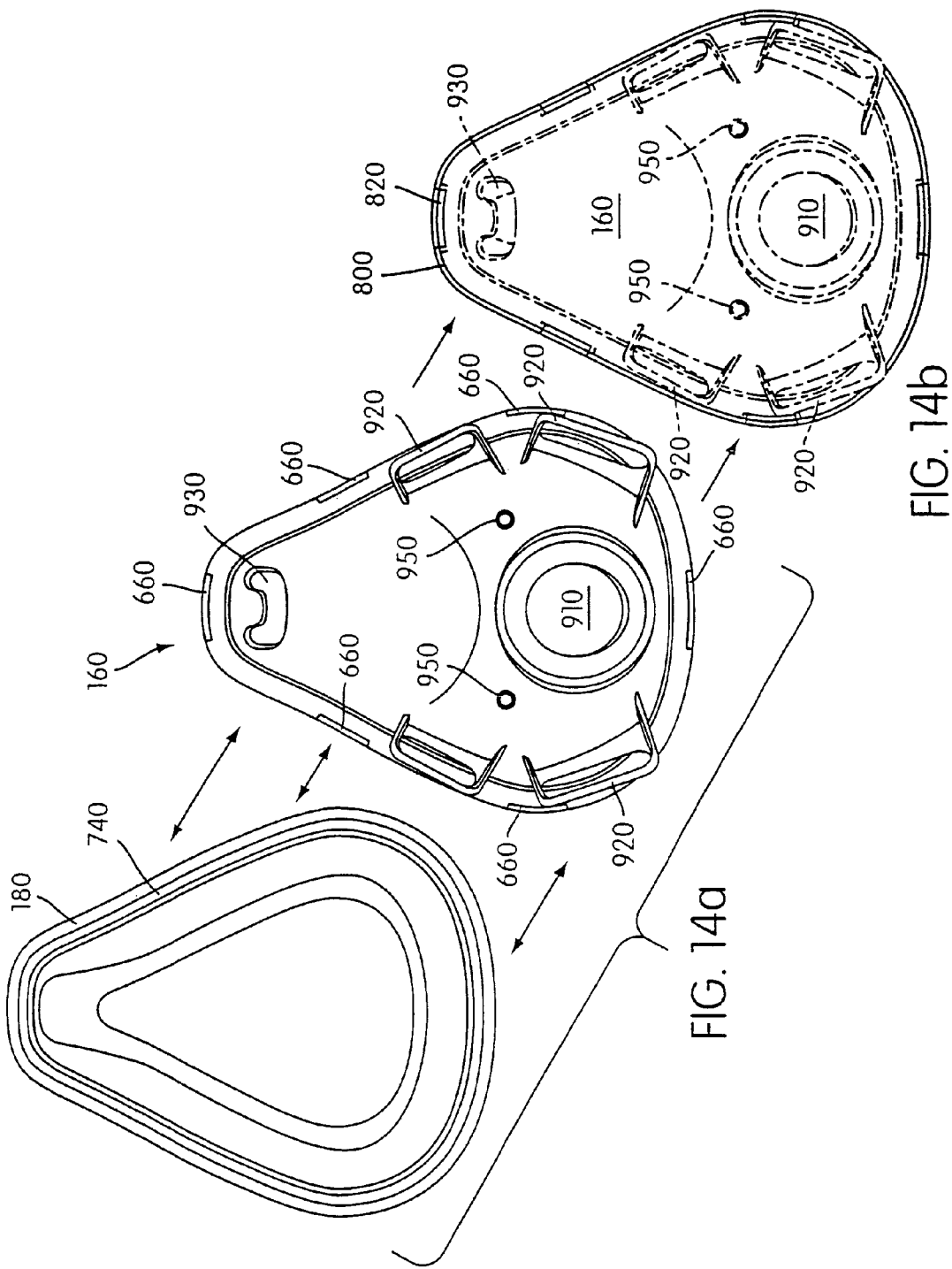
FIG. 14a is an exploded front view of the frame and cushion according to the full face mask.
FIG. 14b is an assembled view of the cushion and frame, along with the clip.
Figure 15:
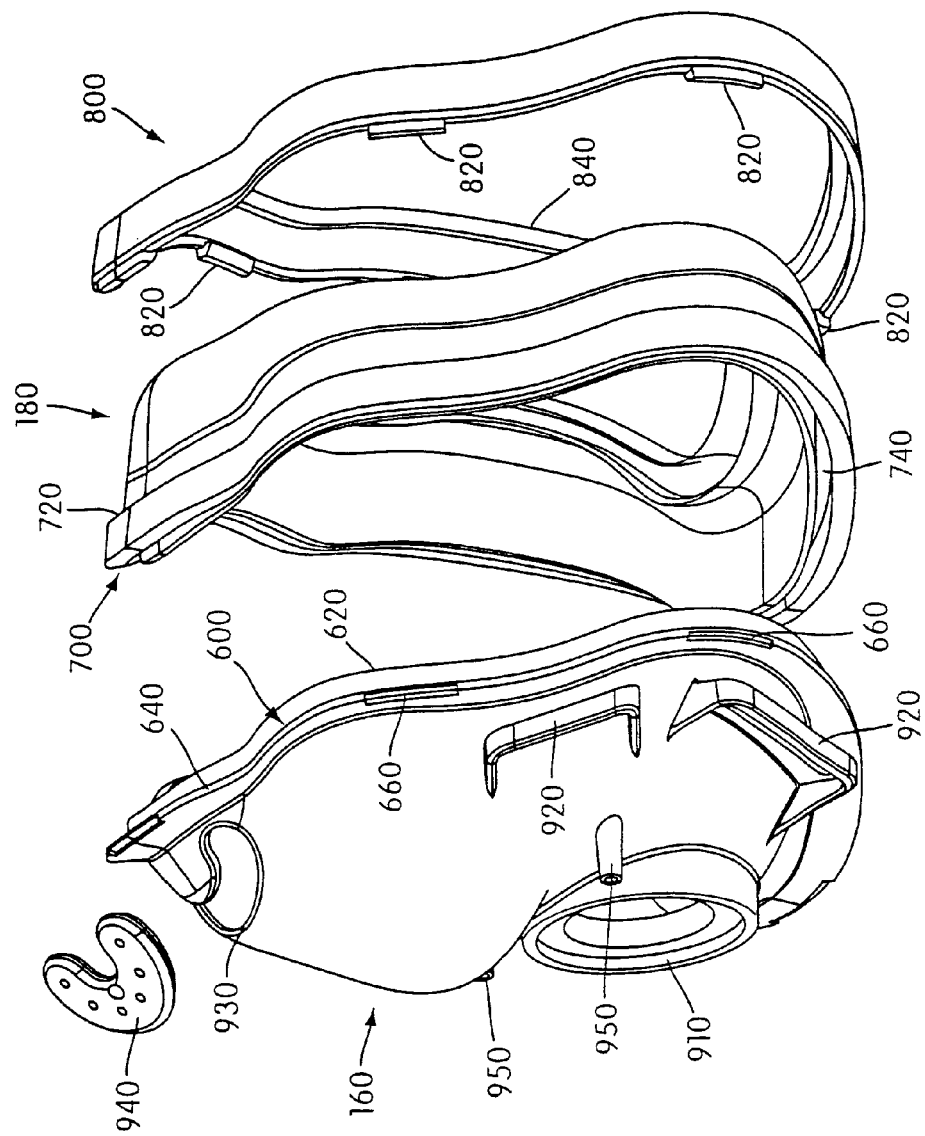
FIG. 15 is an exploded view of an embodiment of the invention as a full-face mask.
Figure 16A:
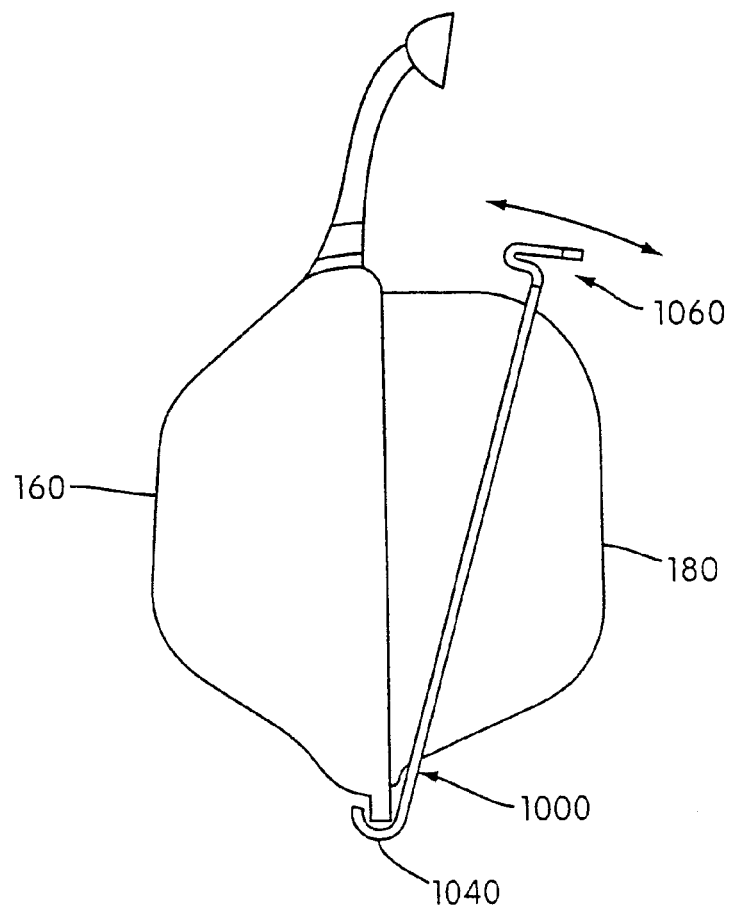
FIG. 16a is a schematic side view of an embodiment employing an alternative clip arrangement.
Figure 16B:
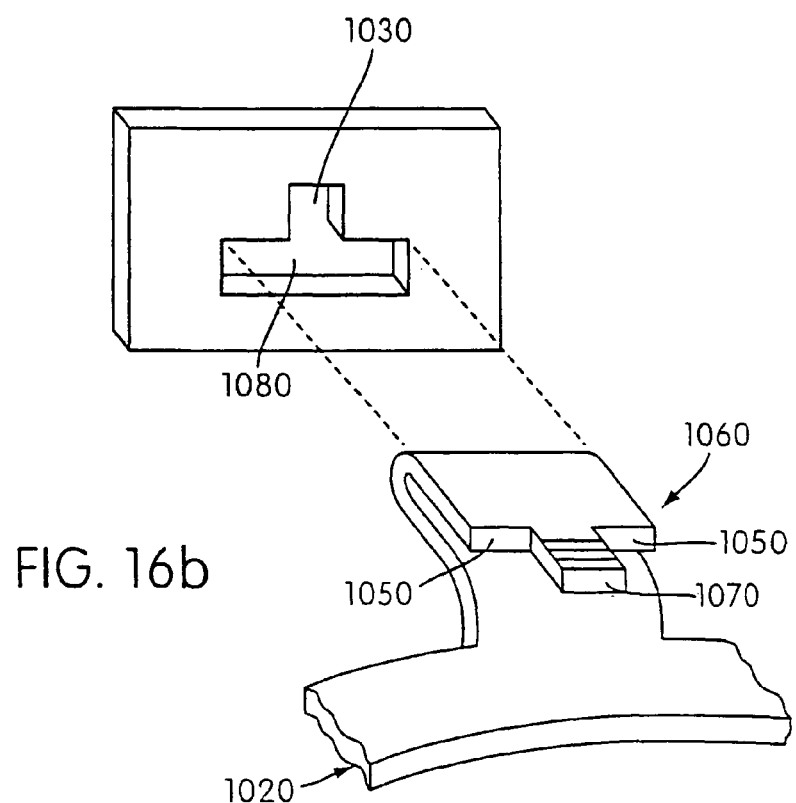
FIG. 16b is a perspective view of engagement of the clip with the mask frame.
Figures 16C, 16D:
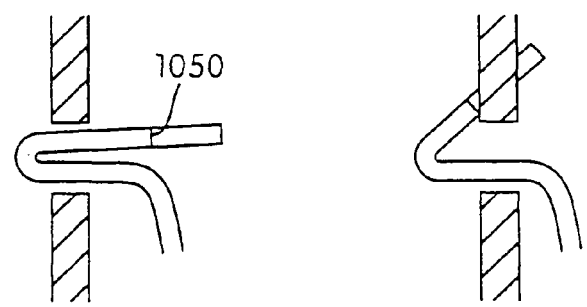
FIGS. 16c and 16d are side views showing clipping of the tab into the slot on the mask frame.

The invention is also suitable for a full-face mask system. FIGS. 8*a*-15 show several exploded views of a Mirage® full-face mask which includes an embodiment of the invention, including a mask frame (160), cushion (180) and clip (800). While FIGS. 8*a*, 9*a*, 10*a*, 11*a*, 12*a*, 13*a* and 14*a* show an exploded view of the frame (160) and the cushion (180), FIG. 15 shows an exploded view including the clip (800) as well; FIGS. 8*b*, 9*b*, 10*b*, 11*b*, 12*b*, 13*b* and 14*b* show the assembled view of the cushion, clip and frame, with the cushion and frame shown in phantom and the clip shown in solid lines. The clip (800) in FIG. 8*b* can be seen to overlie the cushion (180) since a sidewall (801) of the clip (800) instead of the sidewall (181) of the cushion (180) is visible. In addition, at least one of the securing tabs (820) can be seen. In FIGS. 9*a*-12*a* and 14*a*, recesses (660) can be seen on the frame (160), and FIGS. 9*b*-12*b* and 14*b* show the securing tabs (820) which engage with the recesses (660). FIG. 14*b* in particular shows that the clip (800) completely surrounds the frame (160), and each of the securing tabs (820) is positioned within respective recesses (660). FIG. 14*b* also shows that the recesses (660) are slightly larger than the securing tabs (820) in length so as to allow for a small degree of misalignment, to facilitate assembly. The frame is adapted to cover both the mouth and nose region of the patient's face, and includes a gas inlet aperture (910), connection points (920) for headgear straps, an aperture (930) for receiving an air vent (940) (FIG. 15) and ports (950).

The interengagement of the clip (800) and the respective rim portions (600), (700) of the frame (100) and cushion (180) are similar in principle and construction to those described above with reference to FIGS. 5*a* to 5*f* and 7*a* to 7*e*, except there are six angularly spaced tabs (820) and the respective recesses (660). As in the nasal mask assembly, the rim portion (600) of the frame includes a tongue (620) and a lateral flange (650) with recesses in its front surface adjacent its edge, the rim portion (700) of the cushion having a complementary groove (740) and rear shoulder surface (720), and the clip having a flange (840) and securing tabs (820) generally as described above for the nasal mask assembly.

FIGS. 16*a* to 16*d* illustrate an alternative clipping arrangement. The clip (1000) is again formed generally as a collar, with a rear flange (1020) for engaging the shoulder of the cushion as previously described.

At the base of the clip is a securing hook (1040) which hooks over and engages behind the lateral flange of the mask frame (160), allowing the clip to pivot.

At the top of the clip is a resilient detent arrangement (1060), adapted for engagement with an inverted T-shaped slot (1080) on the upper extension of the mask frame (160) as best shown in FIGS. 9*a* to 9*c*.

Figure 1:
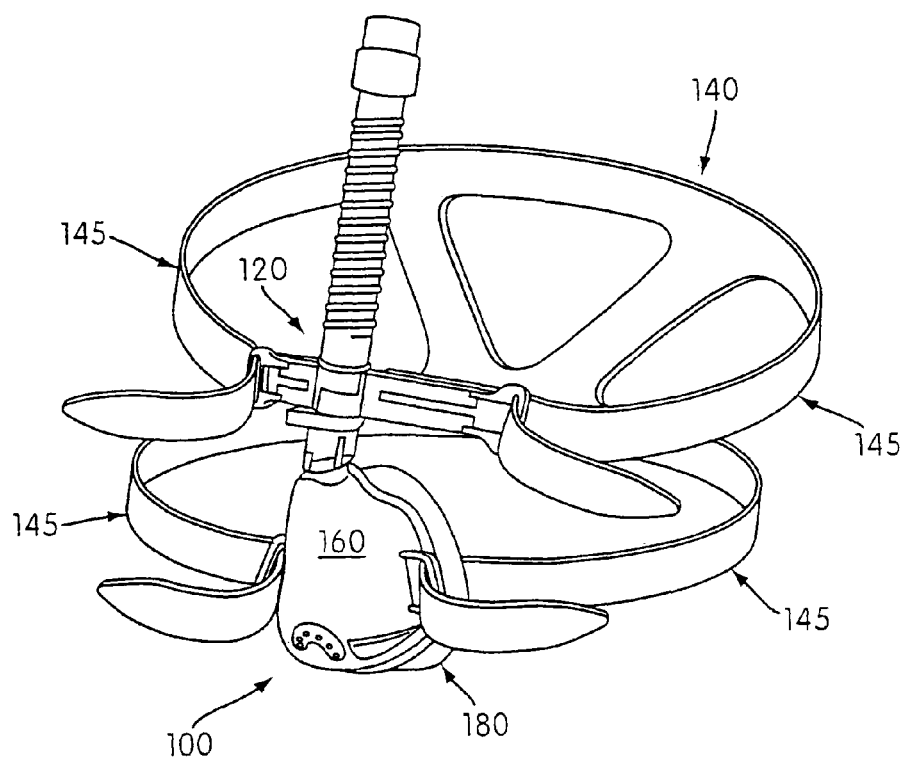
FIG. 1 shows the prior art Mirage® nasal mask system including mask frame, cushion, headgear and forehead support.
Figure 3A:
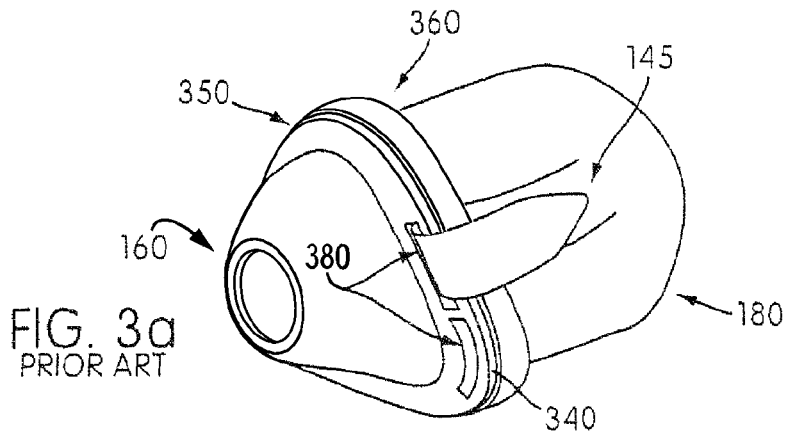
FIG. 3a shows a perspective view of the mask frame and cushion and strap of the prior art ResMed Modular Mask System.
Figure 3B:
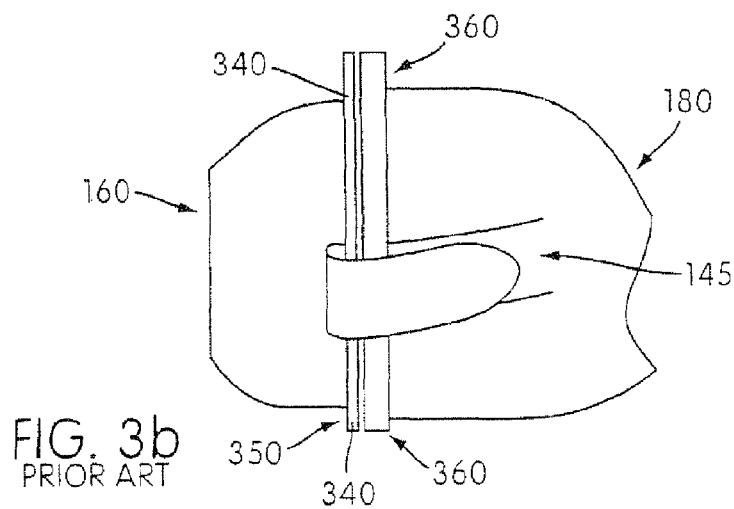
Figure 3C:
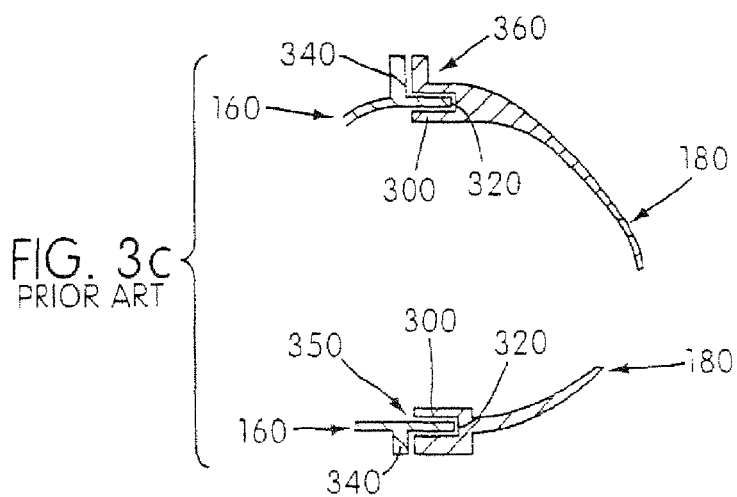
Figure 4A:
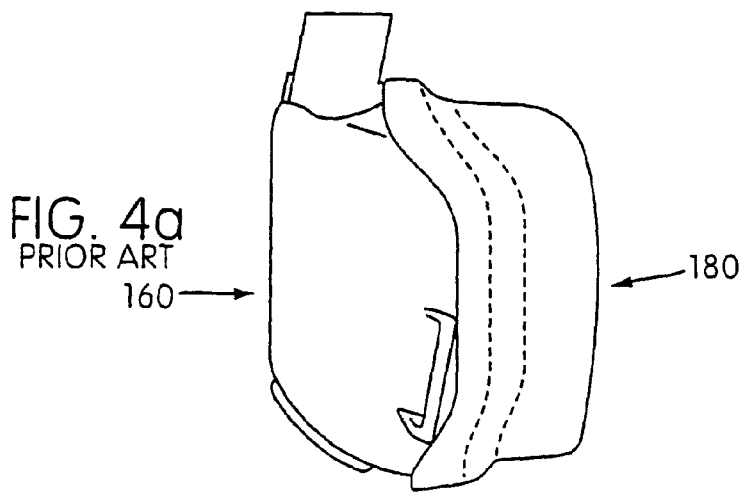
FIG. 4a shows a side view of a prior art mask frame and cushion incorporating a tongue and groove mechanism with an irregular cross-section.
Figure 4B:
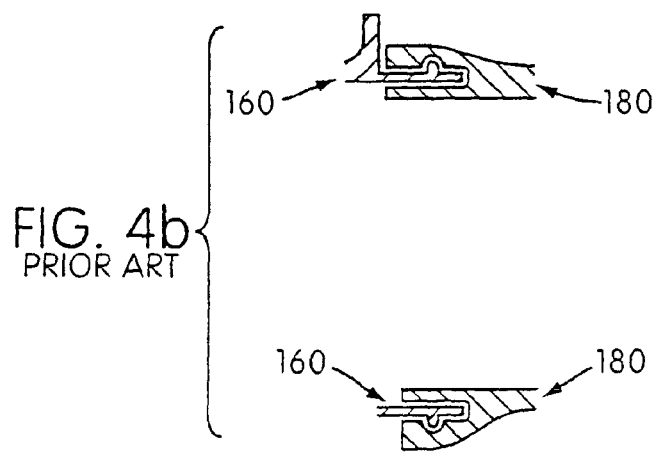
FIG. 4b shows a cross-sectional detail of the mask shown in FIG. 4a where the cushion is secured to the frame.
Figure 4C:
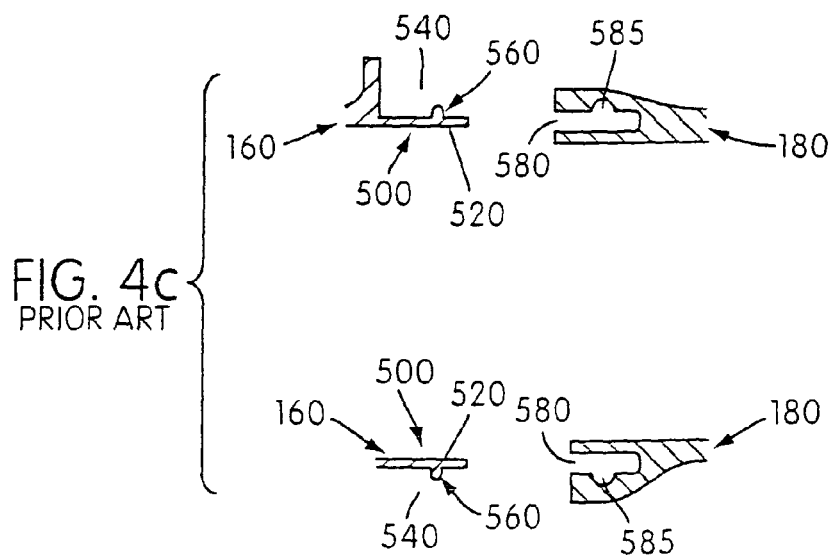
FIG. 4c shows a similar cross-sectional detail of the mask shown in FIG. 4a where the 20 cushion is not secured to the frame.

As shown, the detent is formed as a resilient U-shape with rearwardly facing shoulders (1050) on either side of a narrow tab (1070). In use, the clip is pivoted to force the U-shaped detent through the wide part of the T-slot (1080), until the shoulders (1050) clear the rear surface of the slot. The resilience of the detent then forces tab (1070) into the leg (1030) of the T-slot, to retain the clip in position. To disengage the clip, the tab (1070) is depressed to allow the detent to pass back through the slot In an unillustrated embodiment of the invention, the tongue and groove of the frame and cushion have an irregular cross-section, for example as shown in FIG. 4*a* to 4*c*.

Although the invention has been described with reference to particular embodiments, it is to be understood that these embodiments are merely illustrative of the application of the principles of the invention. Numerous modifications may be made in the illustrative embodiments of the invention and other arrangements may be devised without departing from the spirit and scope of the invention.

The invention claimed is:

1. A respiratory mask assembly for delivering breathable gas to a patient, comprising:
    a substantially rigid mask frame defining a cavity with an opening;
    a silicone mask seal to seal with the patient's face; and
    a plastic clip member detachably engaged with the mask frame so as to retain the mask seal on the mask frame, the clip member being resiliently movable outwards relative to the frame to disengage the clip member from the frame.

2. The respiratory mask assembly according to claim 1, wherein the clip member includes at least one securing tab engageable with the mask frame.

3. A respiratory mask assembly according to claim 1, wherein said mask seal is a nasal seal.

4. A respiratory mask assembly according to claim 1, wherein the mask frame and clip member are made of polycarbonate.

5. A nasal mask assembly comprising:
    a substantially rigid mask frame including at least one first engagement feature;
    a nasal cushion provided to the frame, the nasal cushion and frame, when combined, defining a nasal breathing cavity;
    a plastic clipping structure to secure the cushion to the frame, said clipping structure including at least one second engagement feature that fits over the frame and engages with the at least one first engagement feature of the frame when assembling the cushion to the frame, the clipping structure being resiliently movable outwards relative to the frame to disengage the clipping structure from the frame; and
    a T-shaped forehead support extending from the frame, said forehead support being structured to secure a forehead pad to each lateral side of the T-shape, said forehead support including slots at each end of the T-shape to receive patient headgear.

6. A nasal mask assembly according to claim 5, wherein the clipping structure is of complementary shape to the cushion and frame.

7. A nasal mask assembly according to claim 5, wherein the cushion and frame engage one another via a tongue and groove arrangement.

8. A nasal mask assembly according to claim 7, wherein the tongue is provided to the frame and the groove is provided to the cushion.

9. A nasal mask assembly according to claim 5, wherein the frame and clipping structure comprise polycarbonate and the nasal cushion comprises silicone.

10. A nasal mask assembly according to claim 5, wherein the at least one first and second engagement features include a plurality of first and second engagement features.

11. A nasal mask assembly according to claim 10, wherein one of the first and second engagement features comprises a resiliently deformable detent.

12. A nasal mask assembly according to claim 5, wherein the frame is associated with a slotted point of connection on each lateral side thereof to receive the patient headgear.

13. A nasal mask for delivery of breathable gas to a patient for treatment of sleep disordered breathing, comprising:
    a substantially rigid mask frame made of transparent polycarbonate or similar transparent plastics material, the frame having a front gas inlet aperture,
    the frame having an apex and left and right lateral portions depending from the apex, as well as a bottom portion, opposite the apex, that connects the lateral portions,
    the frame being structured and configured to cover the patient's nose, the frame including a cavity including a rear opening opposite to the front gas inlet aperture,
    the frame having a frame rim surrounding the rear opening and being configured to follow a locus approximating contours of the patient's face,
    the frame having a plurality of first interlocking structures located along the rim of the frame in discretely spaced locations, the plurality of first interlocking structures being located at the left lateral portion of the frame, the right lateral portion of the frame, and the bottom portion of the frame,
    the frame having a lower pair of strap connection points,
    the frame having an extension to support a forehead support, the forehead support having a bridge portion with two spaced apart forehead pads, the forehead support including an upper pair of strap connection points,
    headgear having a pair of lower straps to connect to the lower pair of strap connection points and a pair of upper straps to connect to the upper pair of strap connection points,
    a cushion made of silicone or other material that is relatively soft compared to the frame, the cushion having a shoulder and a cushion rim,
    a clip made of polycarbonate or similar plastics material, the clip having a complementary shape to the cushion rim and the frame rim, the clip being structured to fit over the cushion rim and the frame rim, and
    the clip having a plurality of second interlocking structures to interlock with the plurality of first interlocking structures located at the frame, the frame having a receiving space located radially outward of the frame rim, the receiving space being positioned above the apex and adjacent the extension, the clip having a guide that aligns with the receiving space to guide the clip into place when the clip is secured to the frame, the receiving space and the guide being separate from the first and second interlocking structures.

14. The nasal mask according to claim 13, wherein the clip has a rear side with an inwards flange to engage behind the shoulder of the cushion.

15. The nasal mask according to claim 13, wherein the clip is resiliently movable outwards relative to the frame to disengage the plurality of first and second interlocking structures relative to one another.

16. The nasal mask according to claim 15, wherein the clip and the cushion are separately attachable to the frame.

17. A respiratory mask for a patient, comprising:
    a substantially rigid mask frame,
    the frame having a rim including an apex, left and right lateral portions depending from the apex, as well as a bottom portion, opposite the apex, that connects the lateral portions,
    the frame being structured and configured to cover at least the patient's nose,
    the frame having a plurality of first interlocking structures located along the rim of the frame in discretely spaced locations, a cushion including material that is relatively soft compared to the frame, a clip made of resilient plastics material, the clip being structured to fit over the frame rim, and the clip having a plurality of second interlocking structures to interlock with the plurality of first interlocking structures located at the frame, wherein the clip is resiliently movable outwards relative to the frame to disengage the clip from the frame.

18. The respiratory mask according to claim 17, wherein the clip has a rear side with an inwards flange to engage behind a shoulder of the cushion.

19. The respiratory mask according to claim 17, wherein the frame has a receiving space located radially outward of the rim and positioned above the apex, and the clip has a guide that aligns with the receiving space to guide the clip into place when the clip is secured to the frame, the receiving space and the guide being separate from the plurality of first and second interlocking structures.

20. The respiratory mask according to claim 17, wherein the frame is a nasal mask frame.

21. The respiratory mask according to claim 17, wherein the frame is an oro-nasal mask frame.

22. The respiratory mask according to claim 17, wherein the clip and the frame are polycarbonate, and the cushion is silicone.

23. A respiratory mask for a patient, comprising:
a substantially rigid mask frame,
the frame having a rim including an apex, left and right lateral portions depending from the apex, as well as a bottom portion, opposite the apex, that connects the lateral portions,
the frame having a breathing cavity structured and configured to cover at least the patient's nose,
the frame having a plurality of first engaging structures located along the rim of the frame in discretely spaced locations, the first engaging structures oriented outwardly away from the breathing cavity,
a cushion including material that is relatively soft compared to the frame,
a clip including resilient plastics material, and
the clip having a plurality of second engaging structures to engage with the plurality of first engaging structures located at the frame, the second engaging structures of the clip being resiliently structured to fit over the frame rim to engage with the plurality of first engaging structures, wherein the clip is resiliently movable outwards relative to the frame to disengage the plurality of first and second engaging structures relative to one another.

24. The respiratory mask according to claim 23, wherein the clip and the frame are polycarbonate, and the cushion is silicone.

25. The respiratory mask according to claim 23, wherein the cushion and the clip are separable.

26. The respiratory mask according to claim 23, wherein the cushion and the clip are separate components.

27. The respiratory mask according to claim 23, wherein the cushion and frame form a seal, with no locking, while the frame and the clip lock relative to one another with substantially no sealing.

28. The respiratory mask according to claim 23, wherein, to disengage the first and second engaging structures, the second engaging structures are forced outwardly against their natural resilience to release from the first engaging structures and to ride over an outer edge of the frame.

29. The respiratory mask according to claim 26, wherein the clip is structured to be anchored at one end of the frame, and pivoted or articulated to connect another end of the frame.

30. A respiratory mask assembly for delivering breathable gas to a patient, comprising:
a mask frame having a first cooperating interlocking structure;
a mask cushion provided to the frame;
a plastic cushion clip to retain the mask cushion on the mask frame, the cushion clip having a second cooperating interlocking structure and being selectively attachable to and detachable from the mask frame, the first and second cooperating interlocking structures interlocking with one another in a cooperating relationship to secure the cushion clip on the mask frame;
an elbow joint provided to the frame and having a swivel tube adapted to connect to a gas delivery conduit;
wherein the first and second cooperating interlocking structures are provided to at least a bottom and left and right sides of the mask frame and cushion clip, and include a tab-recess arrangement in which a plurality of tabs are engageable within respective recesses in interlocking relation to secure the clip to the frame, and wherein the cushion clip is resiliently movable outwards relative to the frame to disengage the plurality of tabs and recesses from one another.

31. A respiratory mask assembly according to claim 30, wherein each tab is resiliently movable.

32. A respiratory mask assembly according to claim 30, wherein the cushion includes an outwardly extending portion received on a rim extending around the periphery of the mask frame.

33. A respiratory mask assembly for delivering breathable gas to a patient, comprising:
a mask frame having a first cooperating interlocking structure;
a plastic cushion clip having a second cooperating interlocking structure and being selectively attachable to and detachable from the mask frame, the first and second cooperating interlocking structures interlocking with one another in a cooperating relationship to secure the cushion clip on the mask frame; and
a seal portion adapted to form a seal on the patient's face and having an outer peripheral portion positioned between the mask frame and the cushion clip so as to seal the seal portion on the mask frame, wherein the cushion clip is resiliently movable outwards relative to the frame to disengage the cushion clip from the frame.

34. A respiratory mask assembly according to claim 33, wherein the first and second interlocking structures include a tab-recess arrangement in which a plurality of tabs are engageable within respective recesses to secure the clip on the frame.

35. A respiratory mask assembly according to claim 34, wherein the first and second cooperating interlocking structures are provided to at least a bottom and left and right sides of the mask frame and cushion clip.

36. A respiratory mask assembly for delivering breathable gas to a patient, comprising:
a mask frame;
a mask cushion; and
a plastic clip member engaged with the mask cushion and structured to interlock with the mask frame,
wherein the mask frame and the clip member include a tab-recess arrangement in which a plurality of securing tabs engage with a corresponding one of a plurality of recesses so as to retain the mask cushion on the mask frame, the tab-recess arrangement provided to at least a bottom and left and right sides of the mask frame and clip member, wherein the clip member is resiliently movable outwards relative to the frame to disengage the clip member from the frame and to allow removal of the mask cushion.

37. The respiratory mask assembly according to claim 36, wherein each of said securing tabs is resiliently movable.

38. A mask assembly comprising:
a mask frame;
a mask seal having a frame-engaging front side including a shoulder portion and a patient-contacting rear side; and
a clip adapted to secure the seal to the frame, wherein the clip includes a body portion engaged with the shoulder portion of the seal such that the shoulder portion of the seal is positioned between the clip and the mask frame,
said frame and clip include a tab-recess arrangement in which a plurality of tabs releasably engage with a corresponding one of a plurality of recesses, wherein the clip is resiliently movable outwards relative to the frame to disengage the plurality of tabs and recesses from one another.

39. A respiratory mask assembly for delivering breathable gas to a patient for treatment of sleep disordered breathing, the assembly comprising:
a substantially rigid mask frame defining a cavity;
a mask cushion comprising a soft material relative to the frame, and adapted to space the frame away from the patient's face; and
a clip member detachably and resiliently engaged with the mask frame so as to retain the cushion on the frame, the clip member comprising polycarbonate or similar material,
wherein the frame includes a first interlocking feature and the clip member includes a second interlocking feature that releasably and resiliently engages with and disengages from the first interlocking feature,
wherein the clip member is resiliently movable outwards relative to the frame to disengage the first and second interlocking features from one another, and wherein the clip member includes a guide located at an apex of the clip member, and the frame includes an extension extending outward from an apex of the frame, the guide aligning with and cooperating with a portion of the extension to guide the clip member into place as the clip member is being secured to the frame, the extension and the guide being separate from the first and second interlocking features.

40. The respiratory mask assembly according to claim 39, wherein the clip member is forcibly movable against its natural resilience relative to the frame to disengage the clip member from the frame.

41. The respiratory mask assembly according to claim 39, wherein the clip member is structured to fit over the cushion and an outer perimeter of the frame.

42. The respiratory mask assembly according to claim 39, wherein the cushion and frame form a seal, with no locking, while the frame and the clip member lock relative to one another with substantially no sealing.

43. The respiratory mask assembly according to claim 39, wherein the first and second interlocking features include a plurality of first and second interlocking features.

44. The respiratory mask assembly according to claim 43, wherein the second interlocking features of the clip member are resiliently structured to fit over the frame to engage with the plurality of first interlocking features.

45. The respiratory mask assembly according to claim 43, wherein the plurality of first interlocking features are located along the frame in discretely spaced locations, the plurality of first interlocking features being located at the left lateral portion of the frame, the right lateral portion of the frame, and the bottom portion of the frame, and wherein the plurality of second interlocking features are adapted to releasably interlock with the plurality of first interlocking features.

46. The respiratory mask assembly according to claim 43, wherein, to disengage the first and second interlocking features in use, the second interlocking features are forced outwardly against their natural resilience to release from the first interlocking features and to ride over an outer edge of the frame.

47. The respiratory nasal mask assembly according to claim 43, wherein one of the first and second interlocking features comprises a resiliently deformable detent.

48. The respiratory mask assembly according to claim 39, wherein the clip member and the cushion are separately coupled to the frame.

49. The respiratory mask assembly according to claim 39, wherein the cushion and the clip member are separate components.

50. The respiratory mask assembly according to claim 39, wherein said mask cushion is a nasal cushion structured and configured to cover the patient's nose.

51. The respiratory mask assembly according to claim 39, wherein the clip member is of complementary shape to the frame.

52. The respiratory mask assembly according to claim 39, wherein the frame is associated with a slotted point of connection on each lateral side thereof to receive patient headgear.

53. The respiratory mask assembly according to claim 39, further comprising an elbow joint provided to the frame and having a swivel tube adapted to connect to a gas delivery conduit.

\* \* \* \* \*